(12) United States Patent
Perrow

(10) Patent No.: US 10,463,502 B2
(45) Date of Patent: *Nov. 5, 2019

(54) EXPANDABLE INTERVERTEBRAL DEVICE AND TOOL FOR INSERTING SAME

(71) Applicant: Pioneer Surgical Technology, Inc., Marquette, MI (US)

(72) Inventor: Scott J. Perrow, Ishpeming, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,214

(22) Filed: Jun. 26, 2017

(65) Prior Publication Data

US 2017/0319355 A1    Nov. 9, 2017

Related U.S. Application Data

(63) Continuation of application No. 15/229,972, filed on Aug. 5, 2016, now Pat. No. 9,687,359, which is a
(Continued)

(51) Int. Cl.
*A61F 2/44* (2006.01)
*A61F 2/46* (2006.01)
(Continued)

(52) U.S. Cl.
CPC ............ *A61F 2/4455* (2013.01); *A61F 2/442* (2013.01); *A61F 2/447* (2013.01); *A61F 2/4465* (2013.01);
(Continued)

(58) Field of Classification Search
CPC ...... A61F 2/4455; A61F 2/442; A61F 2/4465; A61F 2/447; A61F 2/4611; A61F 2310/00796; A61F 2002/2835; A61F 2002/30383; A61F 2002/3039; A61F 2002/30401; A61F 2002/30403; A61F 2002/30481; A61F 2002/30482; A61F 2002/30484; A61F 2002/30538; A61F 2002/3055; A61F 2002/30629; A61F 2002/30632; A61F 2002/30774;
(Continued)

(56) References Cited

U.S. PATENT DOCUMENTS 6,193,757 B1 * 2/2001 Foley .................... A61F 2/4455
                                                       623/17.16
9,408,717 B2 * 8/2016 Perrow .................. A61F 2/4455
(Continued)

*Primary Examiner* — Pedro Philogene
*Assistant Examiner* — David C Comstock
(74) *Attorney, Agent, or Firm* — Fitch, Even, Tabin, & Flannery LLP

(57) ABSTRACT

An expandable interbody device for implantation within an intervertebral space is provided, together with methods and tools for use therewith. The interbody devices include a leading first and trailing second bearing member configured to expand laterally via connecting portions disposed at the trailing end of the first being member and at least the leading end of the second bearing member. In some forms, the connecting portions have an arcuate configuration. The insertion tool is configured expand the interbody device by holding the first bearing member while shifting the second bearing member.

33 Claims, 28 Drawing Sheets

Related U.S. Application Data continuation of application No. 14/509,725, filed on Oct. 8, 2014, now Pat. No. 9,408,717.

(60) Provisional application No. 61/888,387, filed on Oct. 8, 2013.

(51) Int. Cl.
*A61F 2/28* (2006.01)
*A61F 2/30* (2006.01)

(52) U.S. Cl.
CPC ..... *A61F 2/4611* (2013.01); *A61F 2002/2835* (2013.01); *A61F 2002/3039* (2013.01); *A61F 2002/3055* (2013.01); *A61F 2002/30383* (2013.01); *A61F 2002/30401* (2013.01); *A61F 2002/30403* (2013.01); *A61F 2002/30481* (2013.01); *A61F 2002/30482* (2013.01); *A61F 2002/30484* (2013.01); *A61F 2002/30538* (2013.01); *A61F 2002/30629* (2013.01); *A61F 2002/30632* (2013.01); *A61F 2002/30774* (2013.01); *A61F 2002/30825* (2013.01); *A61F 2002/30827* (2013.01); *A61F 2002/30828* (2013.01); *A61F 2002/4475* (2013.01); *A61F 2002/4622* (2013.01); *A61F 2002/4623* (2013.01); *A61F 2002/4629* (2013.01); *A61F 2310/00796* (2013.01)

(58) Field of Classification Search
CPC .. A61F 2002/30825; A61F 2002/30827; A61F 2002/30828; A61F 2002/4475; A61F 2002/4622; A61F 2002/4623; A61F 2002/4629
USPC .............. 606/246, 279, 99, 86 A; 623/17.11, 623/17.15, 17.16
See application file for complete search history.

(56) References Cited

U.S. PATENT DOCUMENTS

| | | | | |
|---|---|---|---|---|
| 2009/0143859 A1* | 6/2009 | McClellan | ............ | A61F 2/4455 623/17.16 |
| 2011/0313457 A1* | 12/2011 | Reglos | ............... | A61B 17/3468 606/249 |
| 2013/0184823 A1* | 7/2013 | Malberg | ................ | A61F 2/442 623/17.13 |
| 2013/0310937 A1* | 11/2013 | Pimenta | ................ | A61F 2/4425 623/17.15 |

* cited by examiner

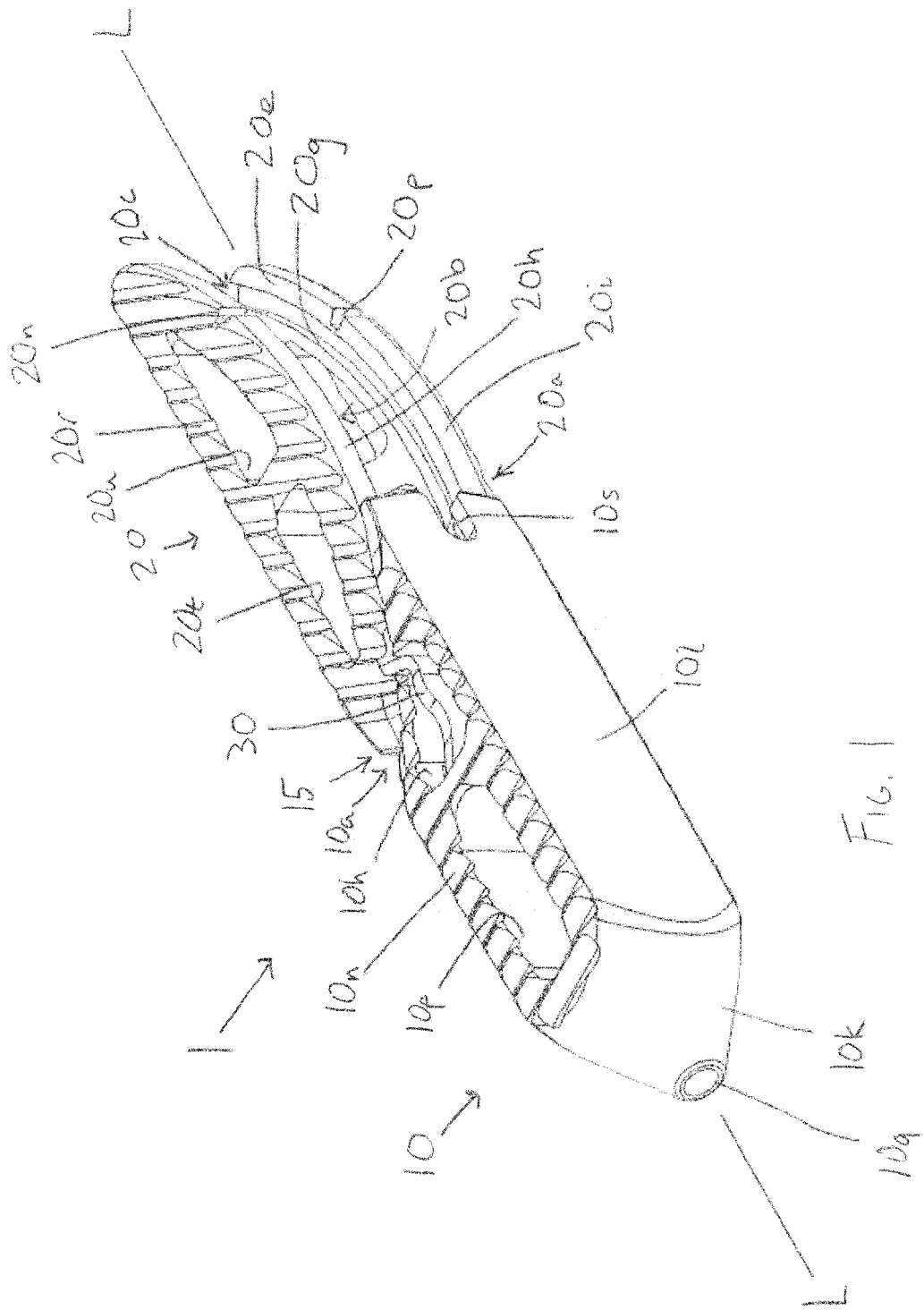

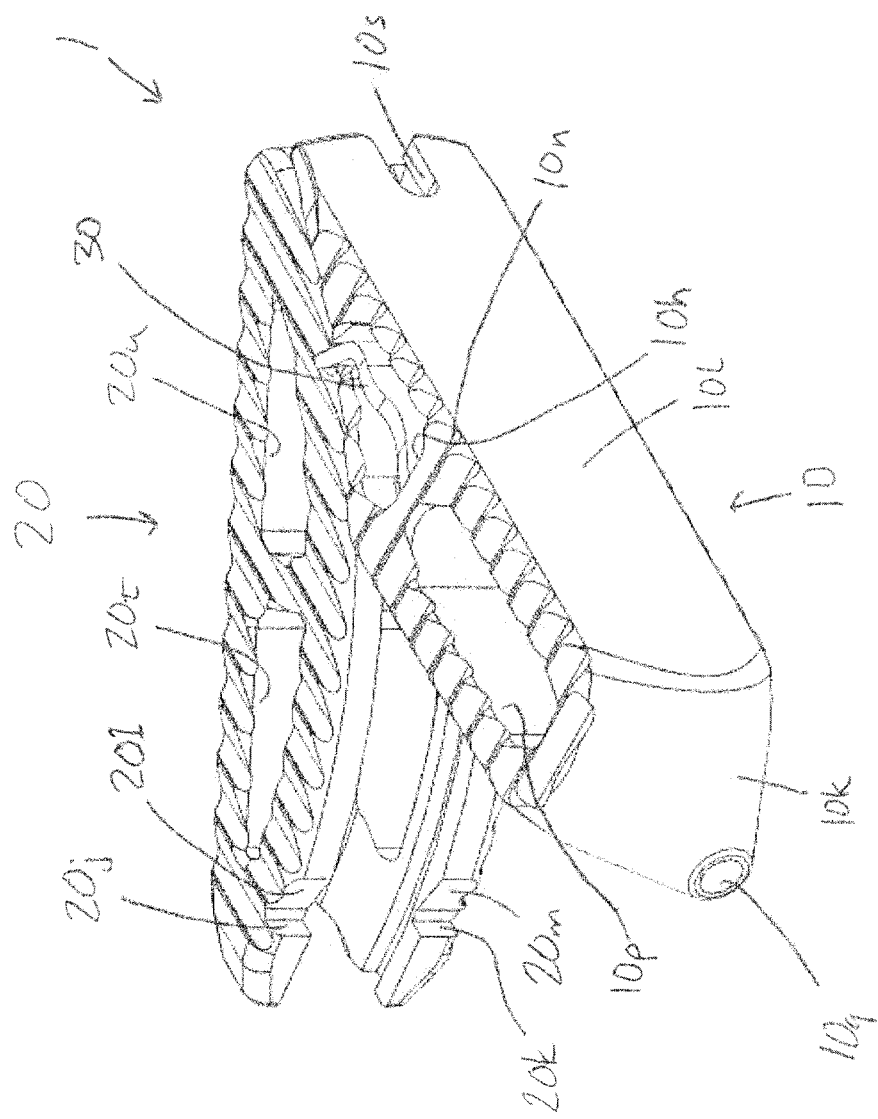

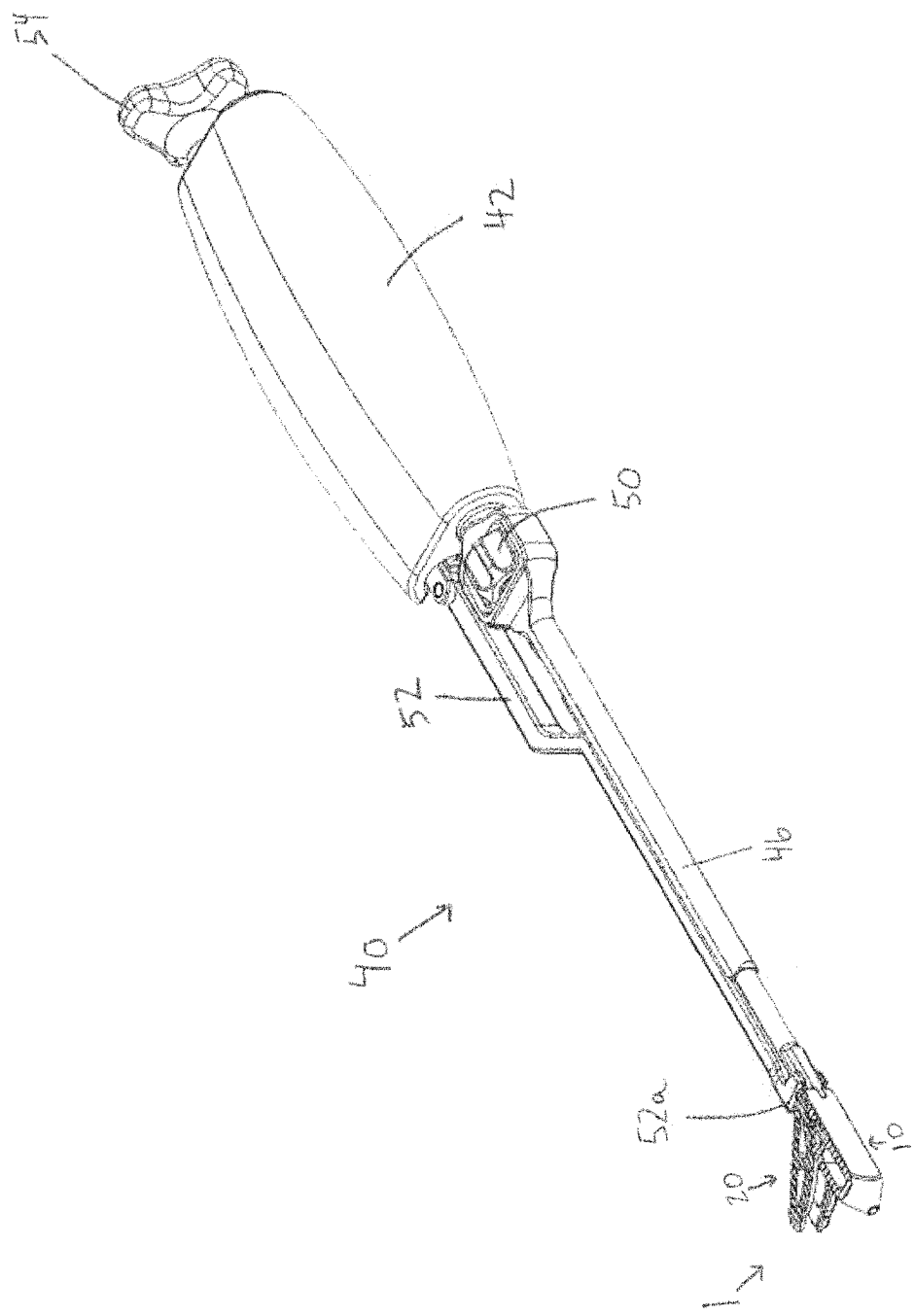

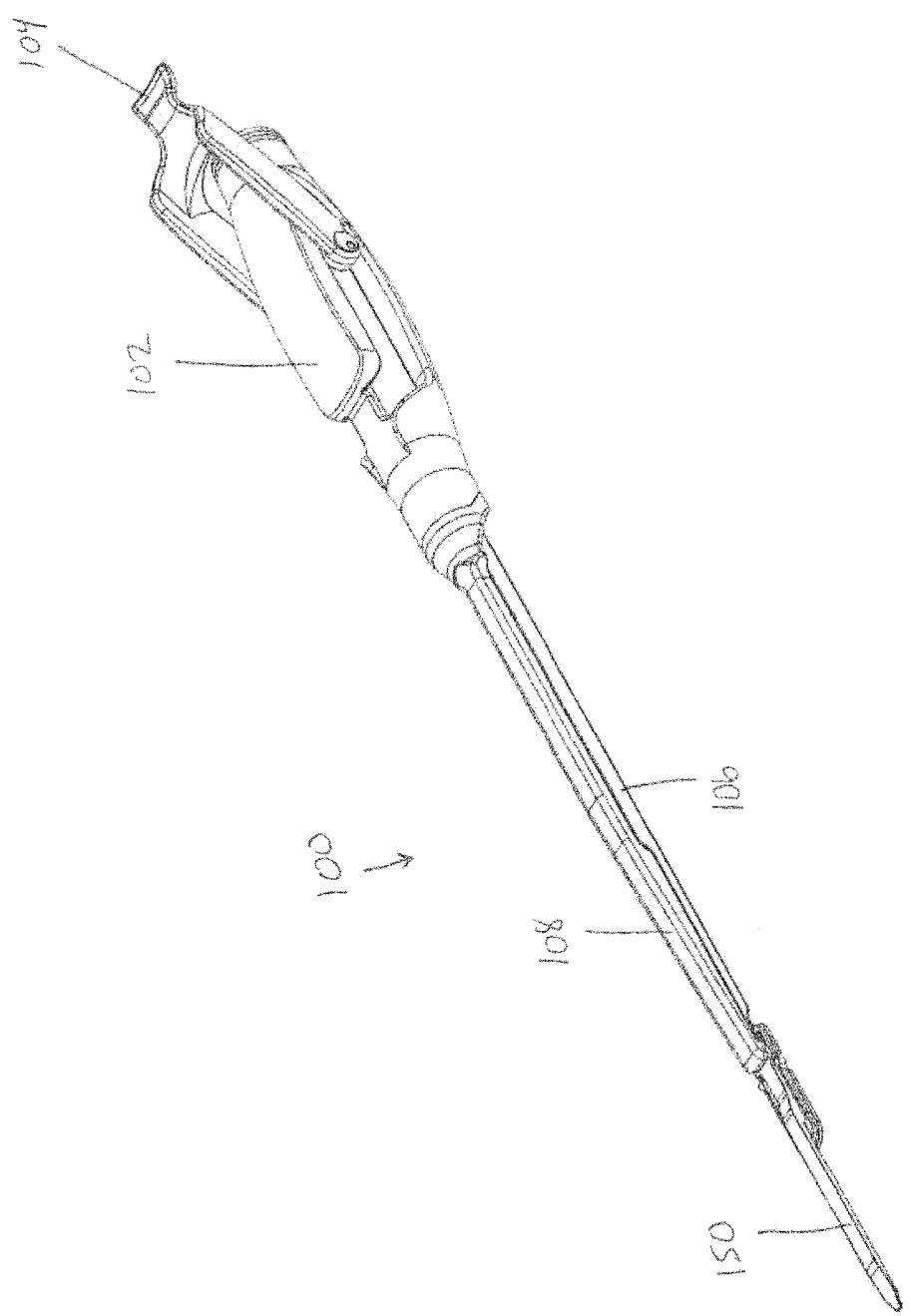

EXPANDABLE INTERVERTEBRAL DEVICE AND TOOL FOR INSERTING SAME

CROSS-REFERENCE TO RELATED APPLICATIONS

This application is a continuation of U.S. patent application Ser. No. 15/229,972, filed Aug. 5, 2016, which is a continuation of U.S. patent application Ser. No. 14/509,725, filed Oct. 8, 2014, now U.S. Pat. No. 9,408,717, which claims the benefit of U.S. Provisional Application No. 61/888,387, filed Oct. 8, 2013, which are all hereby incorporated herein by reference in their entireties.

FIELD OF THE INVENTION

This invention pertains generally to implantable medical devices and, in particular, to expandable implantable devices for intervertebral fusion and/or immobilization and systems and methods for inserting the same.

BACKGROUND OF THE INVENTION

Many people develop back pain during the course of their life due to traumatic injury, disease, or genetic defect. Typically, the patients' intervertebral discs, which support the spine, are damaged, causing the discs to bulge or herniate. The disc bulge then impinges on the nerves of the spine and causes back pain. Surgeons often perform a discectomy to trim the disc bulge to alleviate back pain. However, the discectomy may structurally weaken the disc and often leads to subsequent structural failure of the disc due to wear and aging, once again causing impingement on the nerves of the spine and back pain. Surgical implantation of a medical implant device to structurally support and separate the vertebrae may become desirable to end debilitating back pain and allow patients to regain normal life activities.

One known device for promoting fusion between adjacent vertebrae is an expandable interbody device (IBD). Such devices are generally configured to be inserted into the intervertebral space in a compact configuration, and then are expanded to an expanded configuration to restore the adjacent vertebrae to a desired spacing and provide stability at the affected joint. Numerous mechanisms are known for expanding the lateral size of an expandable IBD. It is also known to provide an IBD with one or more openings in the top and bottom surfaces of the IBD for containing bone graft material to promote fusion between the vertebrae to stabilize the joint.

One disadvantage of known laterally expandable IBDs is that the lateral size may be too large for insertion into the intervertebral disc space from a variety of surgical approaches, limiting the versatility of the IBD. For example, some known expandable IBDs include opposing body portions that are connected via a pivot or rotary hinge at one end and are configured for insertion with the body portions side-by-side. Such a side-by-side configuration is less advantageous or too large for some surgical approaches that have an especially narrow insertion opening.

Another perceived shortfall of known laterally expandable IBDs is maintaining the IBD in the desired expanded position. Some known laterally expandable IBDs lack structure to keep the device from expanding further or retracting after being expanded initially by a surgeon. Because the intervertebral joint is subject to movement, it is desirable for the expandable IBD to be restricted from shifting from the desired expanded configuration after being positioned in the intervertebral space.

A further disadvantage of known expandable IBDs is that it is difficult or impossible to insert bone graft material into or adjacent the expandable IBD after the IBD has been inserted into the intervertebral space. While some expandable IBDs may be configured to hold bone graft material for promoting fusion, once the device is expanded, in some cases there may not be sufficient bone graft material to fill the bone graft cavity in the device such that sufficient bone graft material is kept in contact with the adjacent vertebral endplate to adequately promote bone ingrowth.

SUMMARY OF THE INVENTION

In accordance with one aspect of the invention, an expandable intervertebral device for implantation within an intervertebral space between adjacent vertebrae is provided. The implant device includes first and second bearing or spacer members that are expandable for shifting the members between a compact unexpanded configuration and an expanded configuration. The spacer members are operably connected to one another via connecting portions of the first and second bearing members to allow for shifting of the spacer members with respect to each other. The unexpanded configuration minimizes the lateral width of the intervertebral device to provide ease of insertion of the device into the intervertebral space. The expanded configuration increases the lateral width of the intervertebral device to increase the stability of the joint and further promote fusion of the adjacent vertebrae by increasing the area in which osteoconductive material may be positioned. Although the device may be configured to expand laterally in a range of orientations having a range of lateral widths between the unexpanded and fully expanded configurations, it is generally preferable to fully expand the device to maximize its lateral width. In one form, the interbody device is configured such that insertion and expansion of the device may be accomplished with a single tool.

In one form, the spacer members have an elongate configuration each having a longitudinal axis. In the compact, unexpanded configuration, the longitudinal axes are in substantial alignment with each other in order to minimize the lateral width of the implant to promote ease of insertion. In one form of the expanded configuration, the leading end of the second bearing member is shifted away from the trailing end of the first bearing member so as to be spaced in a lateral direction from the trailing end of the first bearing member. In general, the distance that the leading end of the second bearing member can be spaced in a lateral direction from the trailing end of the first bearing member is constrained in part by the size of the intervertebral space between adjacent vertebrae, including all or part of the annulus if the annulus is present. Accordingly, the bearing members are preferably configured to limit how far the bearing members may be expanded to keep the bearing members from protruding from the intervertebral space. The intervertebral device may include a resilient retaining clip for limiting movement of the second spacer member with respect to the first spacer member.

The first and second bearing members are interconnected by connecting portions that are configured to allow the bearing members to shift between the compact and expanded configurations. In one form, the connecting portions include mating projecting and recess portions of the first and second bearing members that are configured to allow the projecting portion to slide in the recess portion as the second bearing member is shifted relative to the first bearing member. In one form, the connecting portions include a guideway of one of the spacer members and a guide member of the other spacer member with the guide member being guided by the guideway as the spacer members are shifted between the compact and expanded configurations. The guideway can be a channel or track and the guide member can be a projection received in the track. In one form, the track is a cam track having an arcuate configuration so that with the spacer members in the compact, substantially aligned configuration, a force exerted on one of the spacer members generally toward the other spacer member will cause the guide member to slide in the arcuate cam track for shifting the spacer members to the expanded configuration thereof.

The expandable intervertebral device may include a cam surface located on one of the first and second bearing members, and a cam follower surface on the other of the first and second bearing members. The cam surface is configured such that when the first and second bearing members are aligned along their respective longitudinal axes, applying a longitudinally directed force at the trailing end portion of the other bearing member causes the cam follower surface to be cammed against the cam surface so that the leading end portion of the other bearing member is shifted to be laterally offset from the one bearing member. The cam surface in one form is disposed on the trailing end portion of the first bearing member, and the cam follower surface is located on the second bearing member. The cam surface may extend transversely with respect to the longitudinal axis of the one bearing member such that when a longitudinally directed force is applied at the trailing end portion of the other bearing member, the cam follower surface of the other bearing member cams against the transversely extending cam surface so that the leading end portion of the other bearing member is shifted to be laterally offset from the one bearing member. In one form, the cam surface has an arcuate configuration such that the cam follower surface of the other bearing member follows an arcuate path defined by the cam surface when the cam follower surface is cammed against the cam surface to shift the leading end portion of the other bearing member to be laterally offset from the one bearing member. The cam follower surface of the other bearing member may extend from the leading end portion to the trailing end portion thereof such that a portion of the cam follower surface at the leading end portion of the other bearing member engages the cam surface of the one bearing member when the first and second bearing members are substantially aligned along their respective longitudinal axes, and another portion of the cam follower surface at the trailing end portion of the other bearing member engages the cam surface of the one bearing member when the leading end portion of the other bearing member is shifted to be laterally offset from the one bearing member.

In another form, the first and second spacing members each have a longitudinal axis, bone-engaging outer surfaces, a distal leading end, and a proximal trailing end. Connecting portions of the first and second spacer members are configured for allowing the first and second members to stay connected while shifting relative to each other between a narrow insertion configuration and an expanded configuration for stabilizing the joint once inserted therein. In the unexpanded configuration, the spacer members are arranged end-to-end. More specifically, the trailing end or end portion of the first spacer member is engaged with the leading end or end portion of the second spacer member so that the longitudinal axes of the first and second spacer members are substantially aligned or coaxial with one another. In the expanded configuration, the leading end of the second bearing member is shifted away from the first spacer member and the trailing end thereof so as to create a lateral gap between the leading end of the second spacer member and the trailing end of the first spacer member such that the lateral size of the device is increased relative to the narrow insertion configuration and the longitudinal axis of the second spacer member is oriented to be transverse to the longitudinal axis of the first spacer member. In this form, the first and second spacer members cooperate so that the device in the expanded configuration has a V-configuration with the leading ends of each spacer member laterally spaced apart from one another.

In one aspect, the first spacer member has an insertion tool engaging portion at the trailing end thereof and the second spacer member is configured to allow the insertion tool to extend through at least a portion thereof to allow access to the insertion tool engaging portion. The connecting portions may have an arcuate configuration. In another aspect, the connecting portions comprise mating channel portions of the first and second spacer members that are configured to allow the second spacer member to shift along the mating channel portion of the first spacer member. The mating channel portions may have an arcuate configuration to allow the second spacer member to shift along an arcuate path corresponding to the contour of the mating channel portions.

The bearing or spacer members may have a variety of configurations for promoting insertion as well as boney ingrowth once inserted into the intervertebral space. To promote ease of insertion of the intervertebral device, the first spacer member preferably has a tapered leading end. In one form, the first and second spacer members have an opening extending along the longitudinal axes thereof sized and configured to allow a guidewire pass through the spacer members so that the intervertebral device may be inserted into the intervertebral space via the guidewire. In one form, the first and second spacer members include outer surfaces each configured to provide an opening between the respective outer surfaces for inserting osteoconductive material therein to promote boney ingrowth.

Preferably, the outer surfaces of the spacer members include projections to engage with the adjacent, facing vertebral surfaces to keep the spacer members from sliding with respect thereto in at least one direction. In one form, the first spacer member includes projections such as teeth that are configured to resist migration in at least one direction, and the outer surface of the second spacer member comprises projections that are configured to resist migration in a different direction from the projections of the outer surface of the first spacer member. The projections on the spacer members may be configured to allow sliding along the vertebral surfaces when one of the spacer members is shifted from the unexpanded to the expanded configuration, but resist sliding along the path taken by the one bearing member in the opposite direction.

Another form includes a system for implanting an interbody device between adjacent upper and lower vertebrae. The system preferably includes a laterally expandable interbody device having interconnected first and second implant members. The system also preferably includes an insertion tool configured to hold the expandable interbody device. The insertion tool in one form comprises a proximal handle and a distal holding portion of the insertion tool for holding the first implant member of the interbody device. The insertion tool also includes an actuator for engaging with the second implant member for shifting the second implant member at least in part laterally with respect to the first implant member for expanding the interbody device laterally. In one form, a threaded recess is disposed in the body of the first implant member for receiving a mating threaded rod of the distal holding portion of the insertion tool.

The second implant member preferably includes a lateral opening on one side thereof such that the holding portion of the insertion tool may be inserted through the lateral opening to hold the first implant member while allowing the second implant member to be shifted laterally while the first implant member is held by the holding portion. The actuator may be configured to shift proximally and distally along or parallel to a longitudinal tool axis and matingly engage a proximal end of the second implant member to shift the second implant member from an unexpanded orientation to a laterally expanded orientation.

In yet another form, a method of inserting an expandable intervertebral device comprises the steps of preparing an intervertebral disc for implantation of an interbody device, such as by creating an opening in the annulus of the intervertebral disc or removing part or all of the disc for insertion of the interbody device. The intervertebral device may be sized and configured to fit within the boundaries defined by Kambin's triangle, and therefore the opening may be created within those boundaries. The method also may include the steps of inserting the interbody device having interconnected first and second implant members each having a longitudinal axis into the intervertebral space with the longitudinal axes of the implant members in substantial alignment with one another and the first implant member leading the second into the intervertebral space, holding the first implant member with an insertion tool, and expanding the interbody device to an expanded configuration with the insertion tool by shifting the second implant member relative to the first implant member along a path transverse to the longitudinal axis of the first implant member while holding the first implant member.

In one form, expanding the interbody device comprises shifting the second implant member relative to the first implant member along an arcuate path transverse to the longitudinal axis of the first implant member. In another form, the second implant member is shifted relative to the first implant member until a retaining clip of the first member engages in a recess in the second implant member. The step of inserting the interbody device may include threading the interbody device on a guidewire and guiding the interbody device into the intervertebral space therewith. The step of shifting the second implant member relative to the first implant member may include shifting a moveable ram member of the insertion tool along a longitudinal axis of the tool. In another form, the ram member is shifted linearly via rotation of a rotatable knob operably connected to the ram member.

Additional advantages and features of the invention will become apparent from the following description and attached claims taken in combination with the accompanying drawings.

BRIEF DESCRIPTION OF DRAWINGS

To understand the present invention, it will now be described by way of example, with reference to the accompanying drawings in which:

FIG. 1 is a perspective view of an expandable interbody device in a compact configuration in accordance with one aspect of the invention;

FIG. 2 is a perspective view of the interbody device of FIG. 1 in a fully expanded configuration;

FIG. 9A is a perspective view of the interbody device of FIG. 1 held by the insertion tool in the fully expanded configuration;

FIG. 24 is a perspective view of the anchor blade inserter in a full release orientation.

DETAILED DESCRIPTION OF THE PREFERRED EMBODIMENTS

Figure 3:
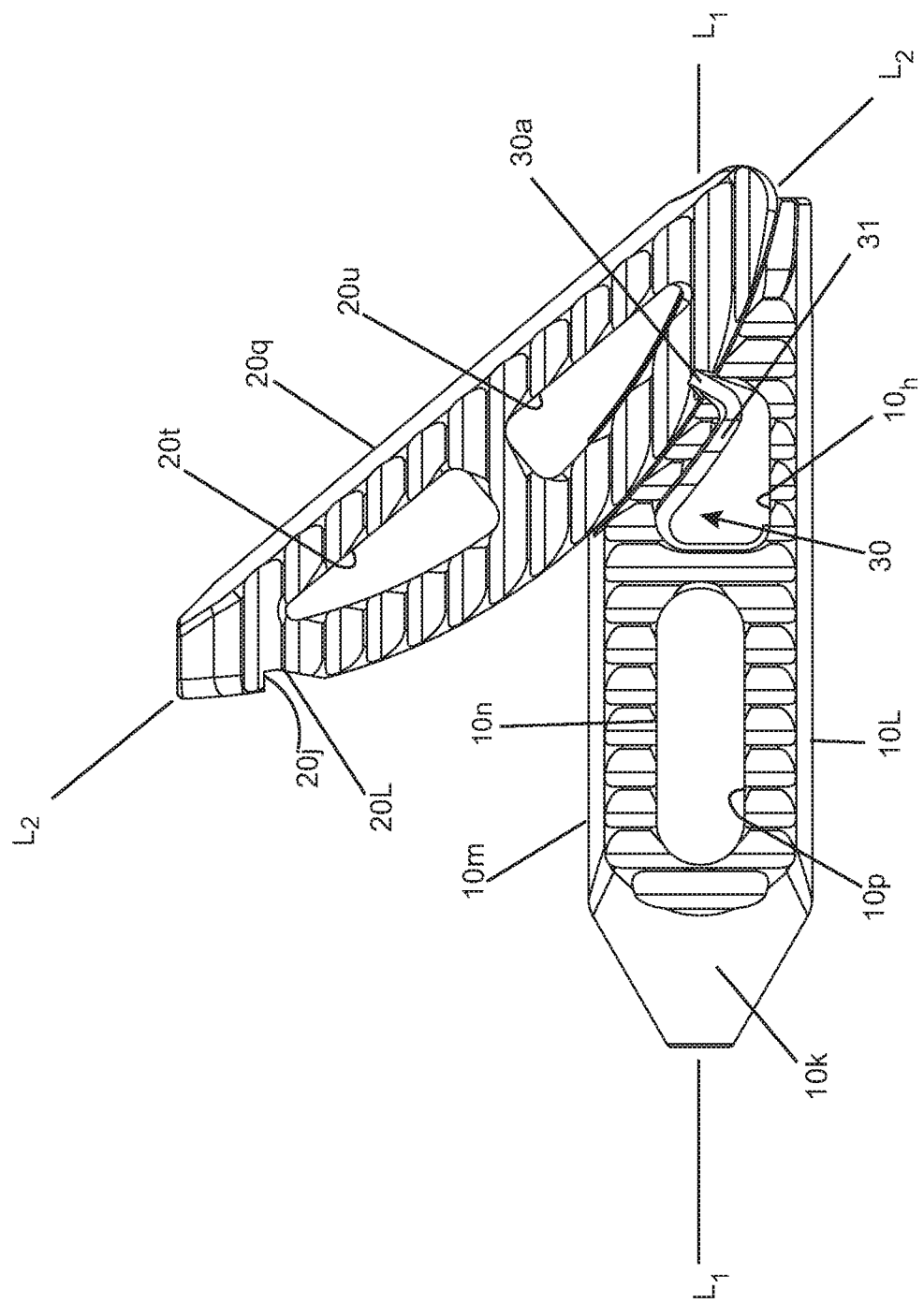
FIG. 3 is top plan view of the interbody device of FIG. 2.
Figure 4:
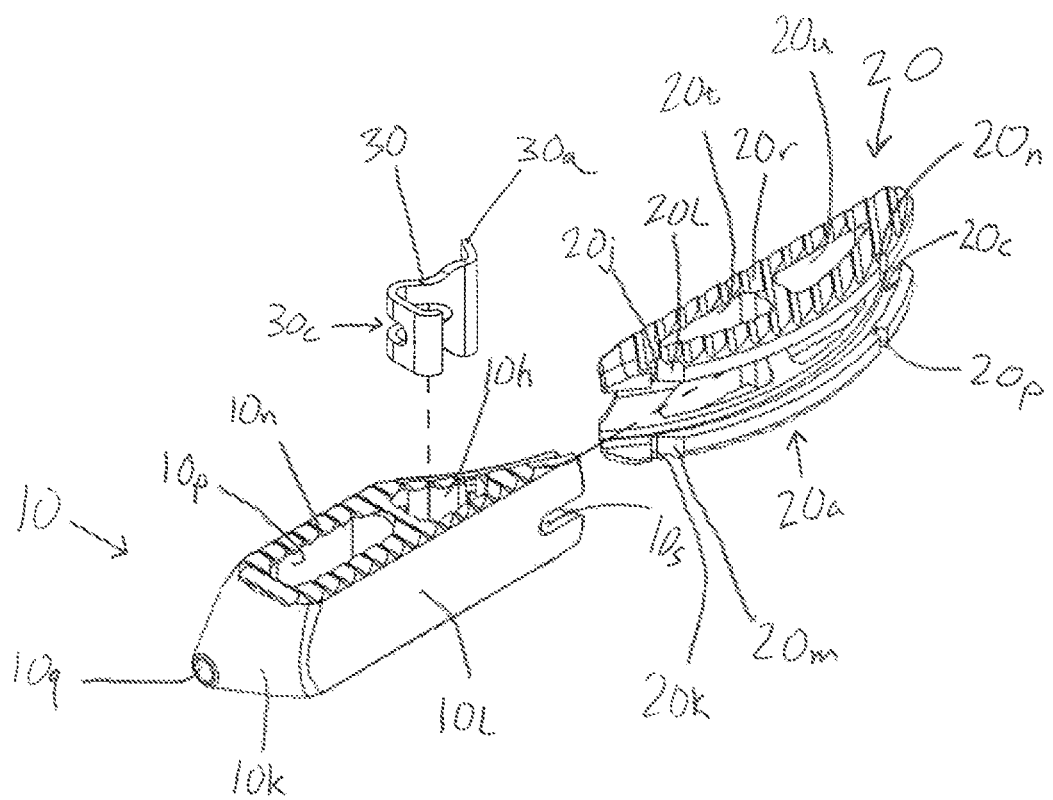
FIG. 4 is an exploded perspective view of the interbody device of FIG. 1.
Figure 5:
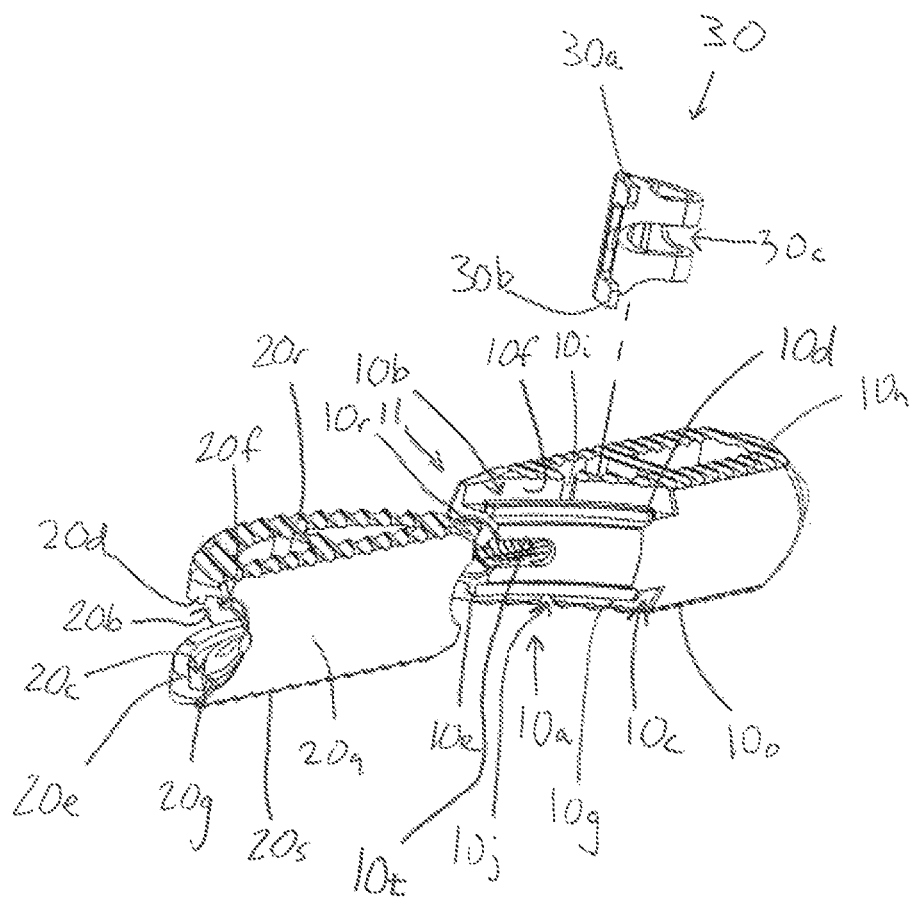
FIG. 5 is an alternate exploded perspective view of the interbody device of FIG. 1.

With reference to FIGS. 1-6 in accordance with one aspect of the invention, an expandable interbody device 1 has first and second bearing or spacer members 10, 20 configured to be implanted in the intervertebral space between adjacent vertebrae (FIGS. 11-13 and 19). The first and second spacer members are movably connected to one another via connecting portions 10a, 20a that form a sliding interface 15 between the spacer members 10, 20. The connecting portions 10a, 20a each have an arcuate configuration to allow the members to be cammingly shifted along an arcuate path with respect to one another. In this regard, the illustrated interface 15 is an arcuate, cam interface 15 comprised of mating cam surfaces and cam follower surfaces that permit the second bearing member 20 to be shifted from an aligned orientation shown in FIG. 1 to a laterally expanded orientation shown in FIG. 2 via a longitudinally directed force along the axis L applied to the trailing end portion 23 of the second bearing member 20. As shown in FIG. 5, the connecting portion 10a includes a wedge-shaped, arcuate trailing end portion 11 having upper and lower channel portions 10b, 10c. The channels 10b, 10c are respectively formed between upper and lower arcuate ridges 10d, 10e and arcuate side walls 10f, 10g.

As shown in FIGS. 1 and 5, the connecting portion 20a of the second spacer member is formed by upper and lower channels 20b, 20c that interengage with channels 10b, 10c and ridges 10d, 10e of the first spacer member. The upper and lower channels 20b, 20c are in turn respectively formed between upper and lower arcuate ridges 20d, 20e and arcuate side walls 20f, 20g, as seen in FIG. 5. Upper arcuate ridge 10d of the first spacer member slides within the upper channel 20b of the second spacer member, and similarly, upper ridge 20d of the second spacer member slides within upper channel 10b of the first spacer member 10. In the same manner, lower arcuate ridge 10e of the first spacer member slides within lower channel 20c of the second spacer member 20, while lower arcuate ridge 20e of the second spacer member 20 slides within lower channel 10c of the first spacer member 10. Although connecting portions in the above described interbody device have an arcuate configuration, other configurations are also contemplated. Similarly, although interengaging channels are illustrated, other structure for connecting and shifting the spacer members 10, 20 is also contemplated.

The expandable interbody device 1 is provided with a motion limiting feature that is configured to limit the range of motion of the first and second spacer members with respect to one another. In the embodiment shown in the figures, the motion limiting feature takes the form of a retaining clip 30 disposed within the body of the first spacer member 10. Retaining clip 30 has a curvilinear or s-shape configuration and is adapted to fit within a through-opening 10h located near the trailing end of the first spacer member 10. The through-opening 10h and retaining clip 30 are sized and configured to allow an engagement portion of the clip 30 to travel between engaged and disengaged positions for respectively retaining the relative positions of the first and second spacer members 10, 20 in the engaged position and allowing the spacer members to shift with respect to one another in the disengaged position. The clip 30 also includes a through opening 30c to allow a guidewire or osteoconductive material to pass through the clip. Preferably, the through-opening is aligned with the guidewire throughbore 30q, described in more detail below. The retaining clip 30 is preferably made from a resilient material, such as titanium or Nitinol®, so that the clip 30 may be biased towards the engaged position. In particular, the clip 30 is configured in such a way as to be biased towards the connecting portion 20a of the second spacer member 20.

The clip engagement portion is disposed at one end of the clip along an arm 31 thereof that includes upper and lower prongs 30a, 30b that are configured to protrude through openings 10i, 10j in the upper and lower arcuate side walls 10f, 10g of the first spacer member 10 such that they engage with the outer facing surfaces 20h, 20i of the upper and lower arcuate ridges 20d, 20e, respectively. Two pairs of stops are disposed in the outer facing surfaces 20h, 20i of the second spacer member to engage with the clip 30 at positions that correspond with a compact insertion configuration and a fully expanded configuration, respectively.

Figure 6:
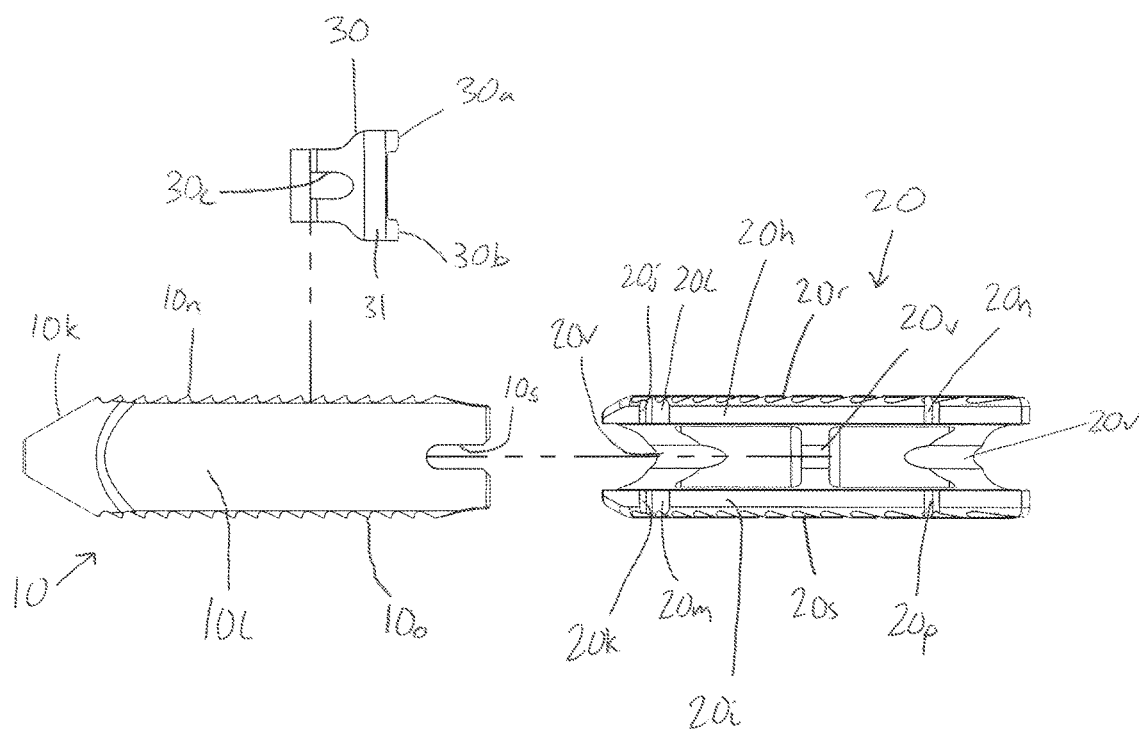
FIG. 6 is an exploded elevational view of the interbody device of FIG. 1.

As shown in FIGS. 4 and 6, the first pair of stops 20j, 20k are located adjacent the leading end of the second spacer member 20 and are configured to keep the second spacer member 20 from moving past its compact insertion position in a proximal direction i.e., opposite to the distal direction which is the direction the second spacer member 20 takes to move to the expanded configuration. However, sloped surfaces 20l, 20m are configured such that they do not provide a blocking surface for clip prongs 30a, 30b and consequently do not block movement of the second spacer member 20 relative to and along the first spacer member 10 in the distal direction. When the second bearing member 20 is shifted distally and laterally along the arcuate path, the clip arm 31 is deflected with the clip prongs 30a, 30b urged against their bias force to be deflected back through the openings 10i, 10j in the upper and lower arcuate side walls 10f, 10g by the sloped surfaces 20l, 20m, allowing second spacer member 20 to be shifted freely. Once the second spacer member 20 is advanced distally and laterally along the arcuate path such that prongs 30a, 30b are aligned with second pair of stops 20n, 20p in the form of grooves adjacent the trailing end of the second spacer member 20, the clip arm 31 will resiliently rebound toward its undeflected orientation so that the prongs 30a, 30b are urged under their bias force into the grooves 20n, 20p. With prongs 30a, 30b disposed in the grooves of stops 20n, 20p, the spacer members 10, 20 are kept from moving with respect to one another in either direction along the arcuate path of the interface 15. Alternatively, the stops 20n, 20p could be configured similar to stops 20j, 20k, which block movement in only the distal direction to provide an outer limit.

Although the clip 30 is shown disposed in the first member 10, it could be alternatively configured to be disposed in the second member 20 and stops for limiting the motion of the spacer members could be provided on the first spacer member 10. Other structures may be used for limiting motion, as would be apparent to one of ordinary skill. Alternatively, the motion limiting features may have an alternate configuration, or be omitted altogether. For example, one or both sets of stops 20j, 20k, 20n, 20p may be omitted. In another form, the clip 30 may be omitted and a motion limiting feature, such as an obstruction near the ends of one or both of the channels 20b, 20c of the second bearing member 20, may be provided to keep the second spacer member 20 from being overextended or separated from the first spacer member 10. Likewise, the motion limiting features may be provided within the one or both of the channels 10b, 10c of the first spacer member.

The first spacer member 10 has a conical or tapered leading end 10k for promoting ease of insertion into the intervertebral space. The first bearing member 10 has opposing lateral sides 10l, 10m, and bone or endplate engaging outer surfaces 10n, 10o. The opposite, lateral sides 10l, 10m each can have a generally flat configuration extending parallel to the axis L1. The outer facing surfaces include through-openings 10p, 10h that extend completely through the body of the first spacer member 10 and may be used to hold osteoconductive material, such as a natural or synthetic bone graft.

The spacer members are cannulated to allow for insertion of guide structure to guide the interbody device into the intervertebral space. A throughbore 10q extends along the longitudinal axis $L_1$ of the first spacer member 10 from the distal leading end to the trailing end. The throughbore 10q extends between the portion of the spacer member that divides the distal through-opening 10p and the proximal through-opening 10h. Because the throughbore 10q extends longitudinally through the entire length of the spacer member 10, it is suitable for insertion of a guidewire to help guide the interbody device 1 into the insertion site. As will be described in more detail herein, the various components of the interbody device 10 are configured to promote boney ingrowth into and through the interbody device for stabilizing the joint after implantation of the device 1.

Figure 17A:
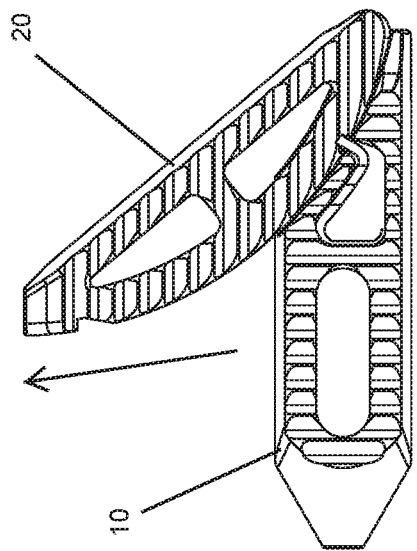
FIGS. 17A-C illustrate the interbody device in the fully expanded orientation.
Figure 17B:
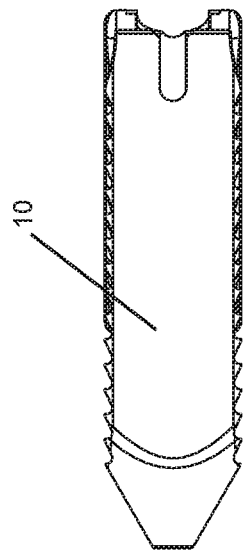
Figure 17C:
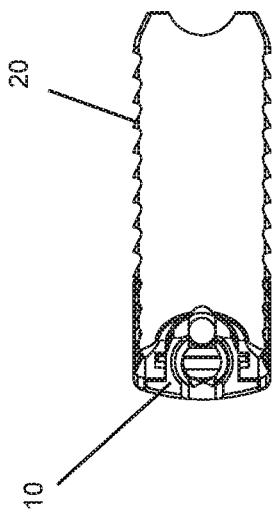
Figure 18B:
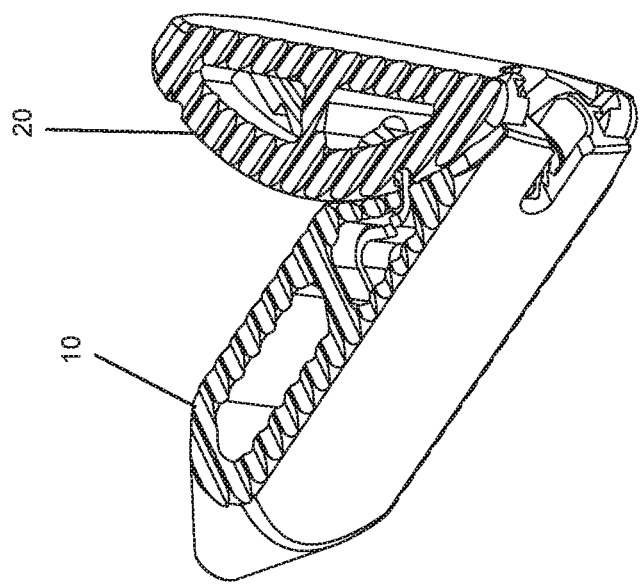
FIGS. 18A and 18B illustrate the interbody device in the compact and expanded orientations, respectively.
Figure 18A:
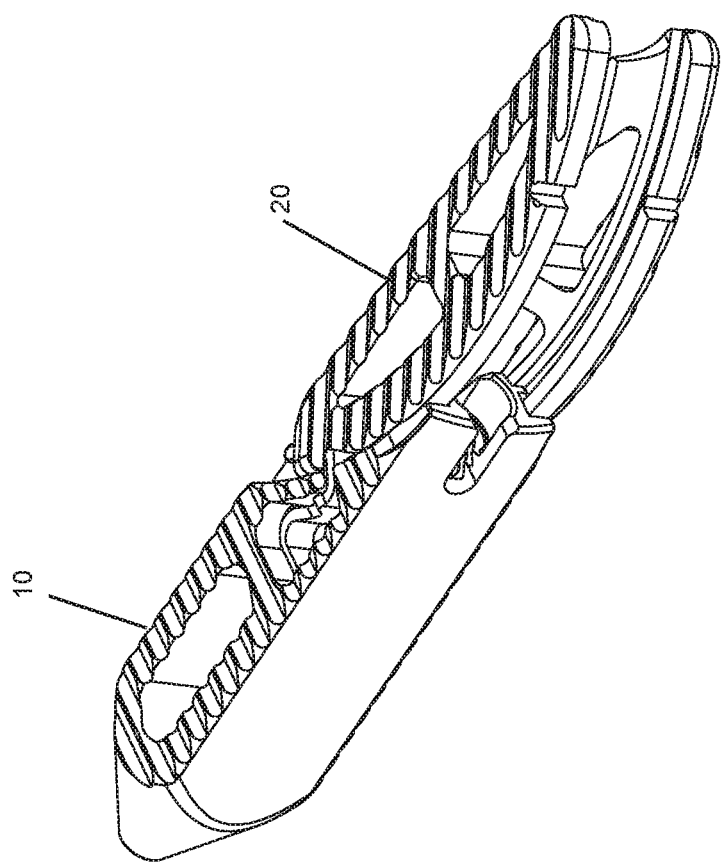
Figure 19:
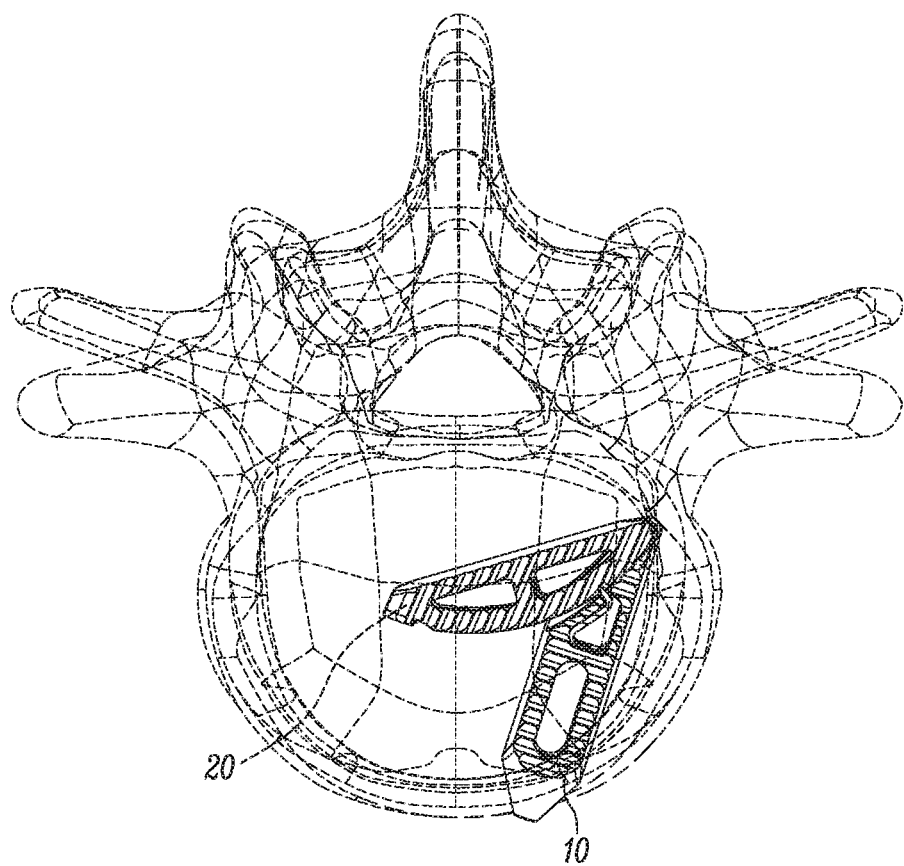
FIG. 19 shows the expanded interbody device implanted within the intervertebral space viewed in the transverse plane.
Figure 20:
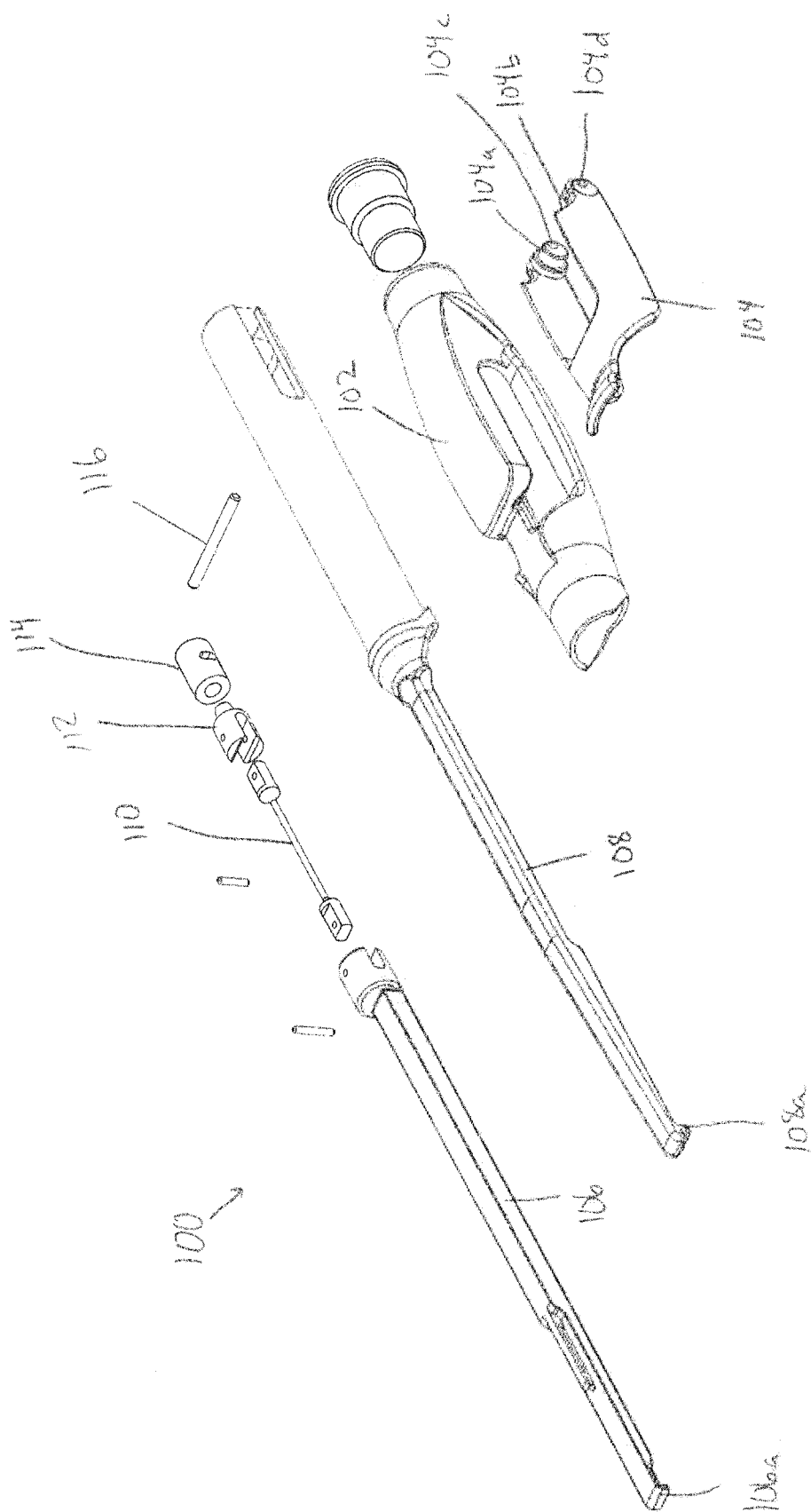
FIG. 20 is an exploded view of an anchor blade inserter in accordance with another aspect of the invention.

As shown in FIGS. 5 and 17C, the first spacer member 10 is provided with a tool engaging portion at its trailing end portion 11. The tool engaging portion includes a threaded recess 10r which has an axis extending therethrough parallel to the longitudinal axis $L_1$ of the spacer member 10 configured for mating with a threaded tool, which will be described in greater detail herein. The throughbore axis of the throughbore 10q is laterally offset from the axis of the threaded recess 10r so as not to cause interference between the guidewire and the insertion tool 40. The tool engaging portion of the first spacer member 10 also includes notched or slotted portions 10s on lateral side wall 10l, and slot 10t opposite slot 10s to provide an index for mating with a corresponding portion of the insertion tool 40. The slots 10s, 10t function to align the interbody device 1 on the tool 40 and prevent rotation of the interbody device 1 relative to the tool while attaching to or detaching from the device 1.

The second spacer member body 20 has a general configuration that resembles a circular segment with an open arcuate side 21 at which the connecting portion 20a is disposed and a generally flat lateral side wall 20q that extends generally parallel to the longitudinal axis $L_2$ of the second spacer member 20. The arcuate side 21 curves convexly or outwardly away from the flat side wall 20q. Upper and lower bone or endplate engaging outer surfaces 20r, 20s include through openings 20t, 20u for promoting boney ingrowth. The arcuate side 21 of the second spacer member has an open configuration such that the insertion tool may be inserted at least partially between the upper and lower outer surfaces to be attached to the proximal trailing end of the first spacer member 10 while allowing the second spacer member to be shifted from its compact insertion position to its expanded position. The inner surface of the second spacer member 20 is also configured to provide clearance for a guidewire when the spacer members are in the compact configuration, the expanded configuration, as well as in intermediate positions between the compact and expanded configurations. As shown in FIG. 6, the second spacer member 20 includes grooves 20v disposed in the inner surface for this purpose.

Figure 1A:
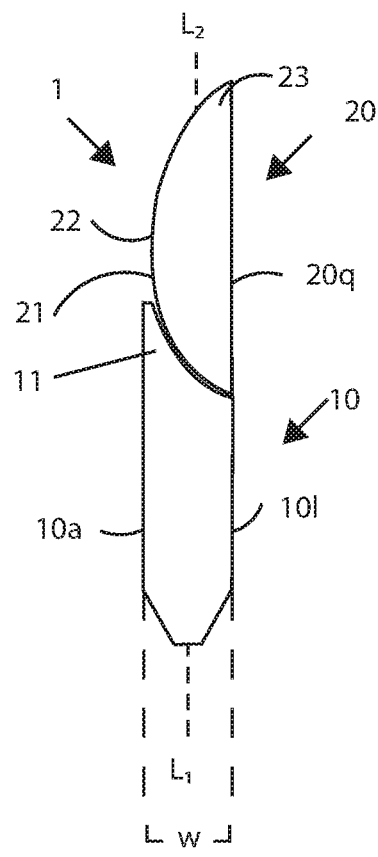
FIG. 1A is a schematic plan view of the interbody device of FIG. 1 in the compact configuration.
Figure 2A:
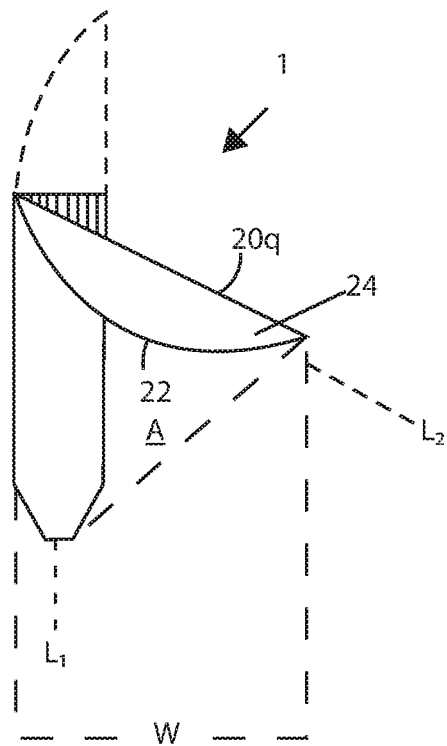
FIG. 2A is a schematic plan view of the interbody device of FIG. 1 in the fully expanded configuration.

Referring next to the schematic views of FIGS. 1A and 2A, it can be seen that the spacer members 10, 20 have a much narrower orientation in the compact, insertion configuration of FIG. 1A than in the expanded configuration of FIG. 2A. More particularly, as illustrated the width, w, of the expandable interbody device 1 in the compact, insertion configuration thereof corresponds to the maximum width of each of the aligned elongate spacer members 10, 20. In this regard, the width w corresponds to the lateral distance between the flat sides 10m, 10l of the spacer member 10 and the lateral distance between the flat side 20q and the point 22 farthest laterally away therefrom along convexly curved side 21. The flat sides 10l, 20q of the spacer members 10, 20 are generally aligned to be flush with one another and the flat side 10m of spacer member 10 is generally aligned with the point 22 along the curved side 21 of the spacer member 20.

To shift the interbody device 1 from the compact configuration to the expanded configuration, the spacer members 10, 20 are shifted relative to each other. To this end, both of the spacer members 10, 20 could be shifted simultaneously, or one of the spacer members 10, 20 can be shifted while the other is held against shifting. The latter approach is described herein, and specifically with respect to holding the spacer member 10 stationary while shifting the spacer member 20, although it will be recognized that substantially the reverse operation could be performed with the spacer member 20 being held while the spacer member 10 is shifted.

As will be described further hereafter, insertion tool 30 advantageously exerts an axially directed force at a trailing end 23 of the spacer member 10. The axially directed force is exerted along the substantially aligned axes L1, L2 with the device 1 in the compact insertion configuration. This provides a mechanical advantage since the input force is applied at a location that is spaced from the cam interface 15 between the interengaging structure of the channels 10b, 10c and 20b, 20c of the spacer members 10, 20 as has been previously described. Further, the trailing end 23 of the spacer member 20 does not significantly shift off of or deviate from the axis along which the input force is directed allowing the input force to be securely transmitted to the spacer member 20 even as it starts to be advanced and turned along the arcuate cam path for being shifted to its expanded orientation. Instead, it is the leading end portion 24 of the spacer member 20 in engagement with the spacer member 10 with the device 1 in the compact configuration that undergoes the greatest amount of shifting away from the axis L1 as the spacer member 20 is turned so that the axis L2 thereof is oriented to extend transversely to the axis L1 of the spacer member 10, as shown in FIG. 2A.

Once the interbody device 1 is shifted to its expanded configuration, the effective width, W, thereof is greatly increased over the width, w, in the compact, insertion configuration. By way of example and not limitation, the effective width, W, in the expanded configuration can be approximately 1.0 inch while in the compact configuration the effective width, w, can be approximately 0.625 inch. In the expanded configuration, referring to the approximate midway point 22, over half of the spacer member 20 including the entirety of the leading end portion 24 extends obliquely away from the arcuate, wedge-shaped trailing end portion 11 of the spacer member 10. This also provides another defined area, A, between the spacer members 10, 20 for receipt of bone growth material. The only effective loss of vertebral engagement area in the widthwise direction of the interbody device 1 over that provided in the compact configuration is the small cross-hatched area shown in FIG. 2A adjacent the trailing ends of the spacer members 10, 20. As is apparent, this is insignificant in size when compared to the extra area of engagement with the vertebral surfaces in the widthwise direction of the interbody device 1 obtained by shifting the spacer member 20 to its expanded position as described above.

The outer surfaces 10n, 10o and 20r, 20s, of the spacer members 10, 20 are preferably configured to resist movement once implanted and to resist expulsion from the intervertebral space. These outer surfaces comprise projections, such as teeth that are configured to resist migration in at least one direction. The teeth on outer surfaces 10n, 10o are oriented to resist movement in the proximal direction along the longitudinal axis $L_1$ while the teeth on outer surfaces 20r, 20s of the second spacer member 20 are oriented to resist movement in a direction transverse to the longitudinal axis $L_2$ of the second spacer member. In particular, the transverse direction corresponds generally to the arcuate path that the second spacer member 20 follows when shifted from the compact position to the expanded position. Accordingly, the teeth of the second spacer member 20 are effective to keep the second spacer member from shifting back from the expanded position to the unexpanded compact position. With this configuration, the teeth simultaneously resist movement in a plurality of directions when the outer bone-engaging surfaces 10n, 10o, 20r, 20s of the spacer members are firmly engaged with the adjacent vertebrae. Alternatively, the projections may be configured to be direction-neutral, or may all be configured to resist movement in the same direction. Other structures known for fixing an implant in the intervertebral space may also be used, such as screws, fins, spikes, deployable or rotatable fixation members, adhesives, and the like.

Any known materials appropriate for implantation into the human body may be used for the interbody device. However, it is preferred to use a polymer such as PEEK for the spacer members 10, 20. Coatings, such as hydroxyapatite (HA), may be used to promote bone growth to the surfaces of the interbody device 1. Other materials may be used, as is well known in the art.

The interbody device 1 is preferably configured to allow for insertion of bone-growth or osteoconductive material, such as natural or synthetic bone grafts, including NANOSS® Bioactive 3D, an advanced bone graft composed of nano-structured hydroxyapatite granules and an open structured engineered collagen carrier in a strip format, available from Pioneer Surgical Technology, Inc. Other biologics may be used, such as NANOSS® Bioactive or NANOSS® Bioactive Loaded, available from Pioneer Surgical Technology, Inc., the latter being a flowable biologic material delivered via a syringe. Other known osteoconductive materials may also be used.

The bone-growth material may be inserted into the cavities of the intervertebral device 1 prior to insertion of the device into the intervertebral space. Alternatively, the bone-growth material may be inserted into the interbody device after insertion of the device into the intervertebral space, either before or after expansion of the spacer members. The trailing ends of the spacer members are sized and configured to provide an access opening that communicates with the interior of the interbody device 1 for inserting osteoconductive material through the access opening. It is also contemplated that osteoconductive material may be introduced in the area A between the first and second spacer members 10, 20 after they are shifted to an expanded configuration, such as shown in FIGS. 2A and 3. A membrane attached to spacer members near the leading ends could be used to maintain the osteoconductive material between the expanded spacer members.

A method of inserting an expandable intervertebral device is shown in FIGS. 10A-13 and includes one or more of the steps of preparing an intervertebral disc for implantation of the expandable interbody device, attaching the expandable interbody device to the insertion tool, inserting the interbody device into the intervertebral space with the insertion tool, expanding the interbody device into an expanded configuration with the insertion tool, removing the insertion tool, and optionally inserting osteoconductive material into or adjacent to the interbody device. In an alternative method, the expandable interbody device is cannulated along a longitudinal axis thereof so that the device may be threaded on a guidewire to guide the interbody device into position within the intervertebral space, with or without use of a separate insertion tool.

An insertion tool 40 is provided for inserting the interbody device 1 into an intervertebral space and for expanding the device after insertion. The interbody device 1 and insertion tool 40 may be sized and configured such that the device 1 may be inserted in many different approaches with respect to the spine, such as anterior, anterolateral, lateral, posterolateral, or posterior approaches. In one preferred method, the device and tool system are sized and configured to implant the device 1 through Kambin's triangle. Kambin's triangle is defined as a right triangle over the dorsolateral disc. The hypotenuse of Kambin's triangle is the exiting nerve root, the base being the superior border of the caudal vertebral body, and the height is the traversing nerve root. (See Park et al., Kambin's Triangle Approach of Lumbar Transforaminal Epidural Injection with Spinal Stenosis, Annals of Rehabilitation Medicine, Dec. 30, 2011.) With such an approach, the intervertebral disc is prepared for implantation by creating an opening in the annulus of the intervertebral disc for insertion of the interbody device within the boundaries defined by Kambin's triangle. Such an approach is advantageous because the device may be implanted without needing to remove any portion of the vertebral bone prior to insertion, simplifying the method of inserting the device and reducing trauma to the patient. With all potential surgical approaches, the disc space may be prepared by removing part or all of the intervertebral disc.

Figure 7:
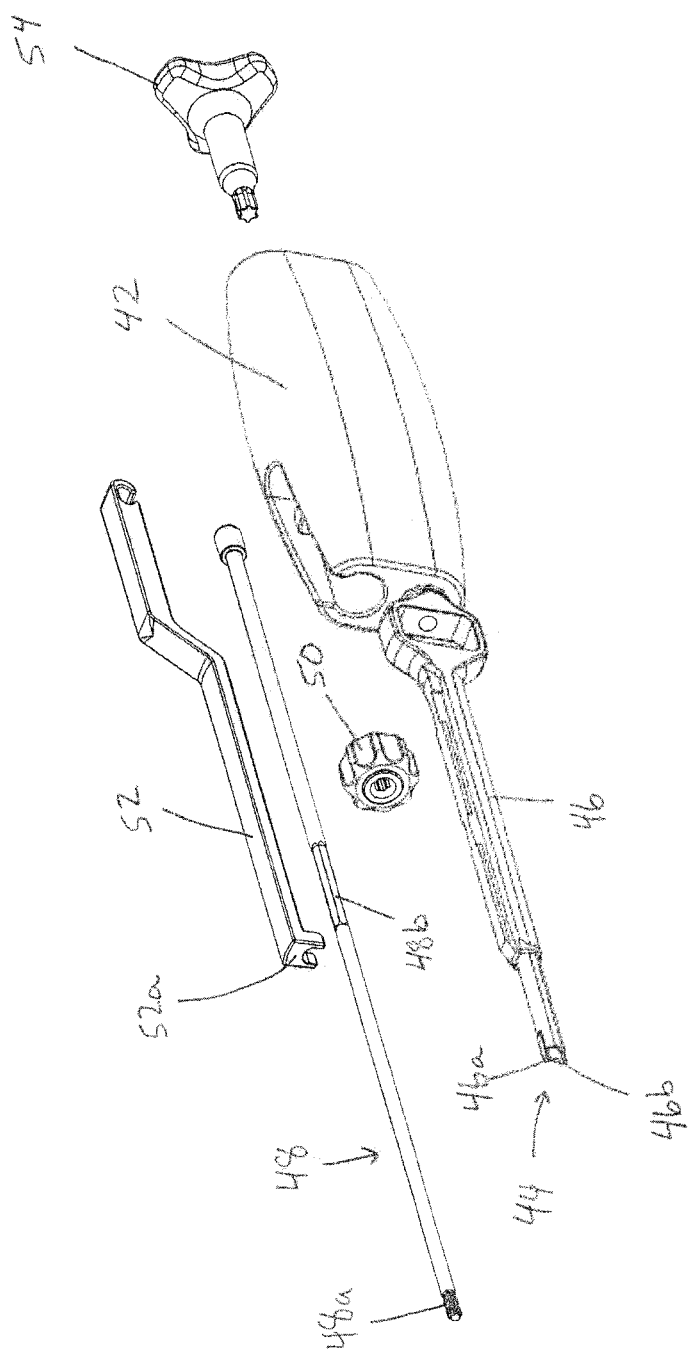
FIG. 7 is an exploded perspective view of an insertion tool for inserting the interbody device of FIG. 1.

As shown in FIG. 7, the insertion tool 40 is comprised of a handle portion 42 at the proximal end of the tool, a distal holding portion 44 for holding the interbody device 1, and an actuator for engaging with the other implant member for shifting the other implant member with respect to the one implant member. The distal holding portion 44 is comprised of a stationary shaft 46 and a draw rod 48 with a threaded end 48a. The draw rod 48 is rotatably disposed within the stationary shaft 46, and is rotatable via a rotatable knob 50 through which the draw rod 48 is mounted. The draw rod 48 includes an indexed portion 48b for matingly engaging with the knob 50. The stationary shaft 46 includes a distal alignment feature in the form of prongs 46a, 46b for engaging with mating slots 10s, 10t. (See FIGS. 1 and 5.) The actuator includes a ram member 52 which is configured to shift distally and proximally along the stationary shaft 48 to engage with the trailing end of the second implant member 20 with the distal end 52a of the ram member 52. As shown in FIG. 8B, the ram member 52 is driven via a threaded drive shaft 53 configured to shift axially along a tool axis LT. The threaded drive shaft 53 is driven via rotary motion provided by rotation of the drive knob 54, which is connected to the proximal end of the drive shaft 53. The drive shaft 53 resides within a partially threaded through-opening 42a of the handle 42. The stationary shaft 46 is connected to the handle 42 via a cap member 56, which resides in through-opening 42b in the handle 42. Cap member 56 threadingly engages with stationary shaft 46 and also includes a through-opening 56a through which draw rod 48 extends and is rotatably supported.

Figure 8A:
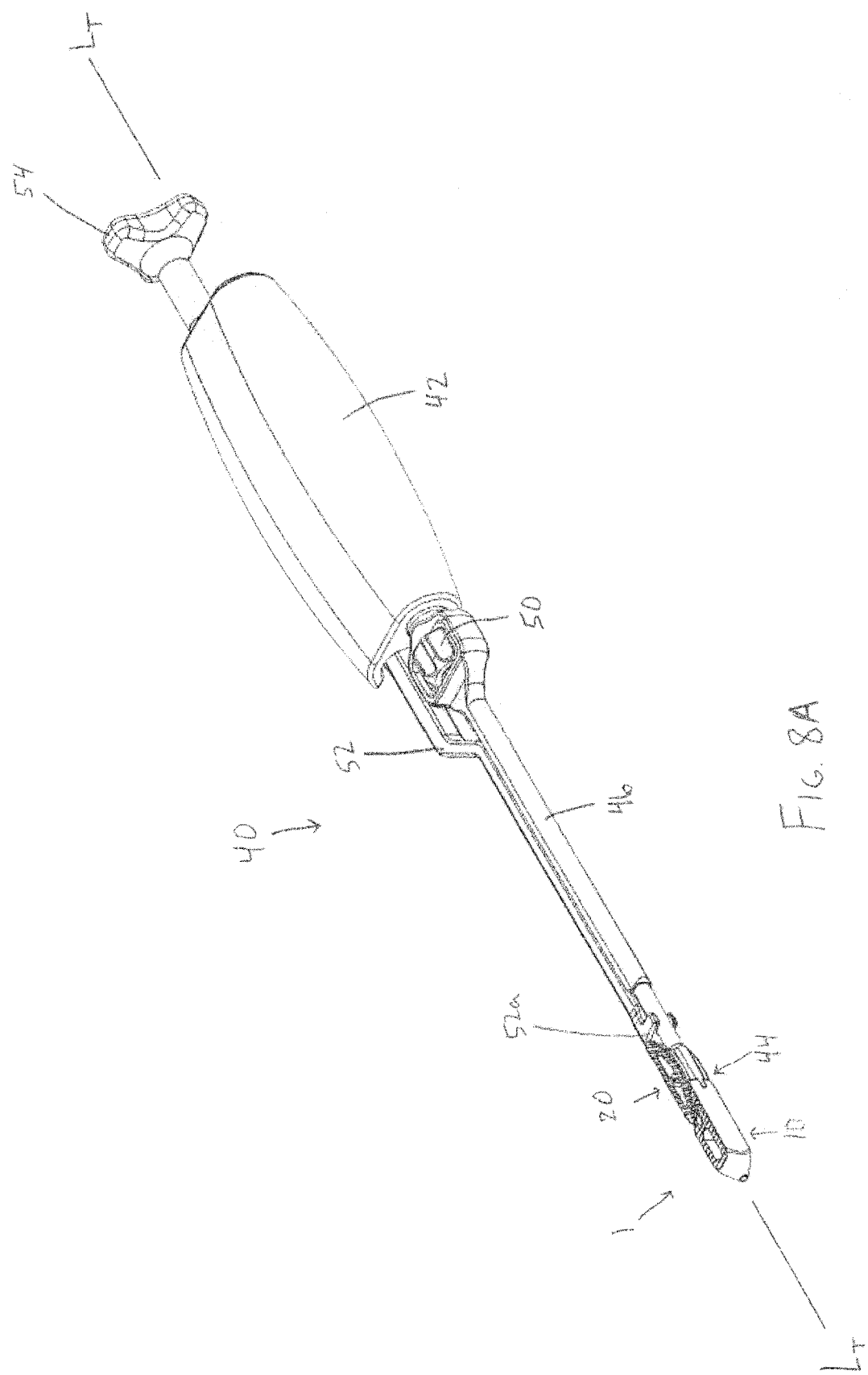
FIG. 8A is a perspective view of the interbody device of FIG. 1 held by an insertion tool in accordance with another aspect of the invention.
Figure 8B:
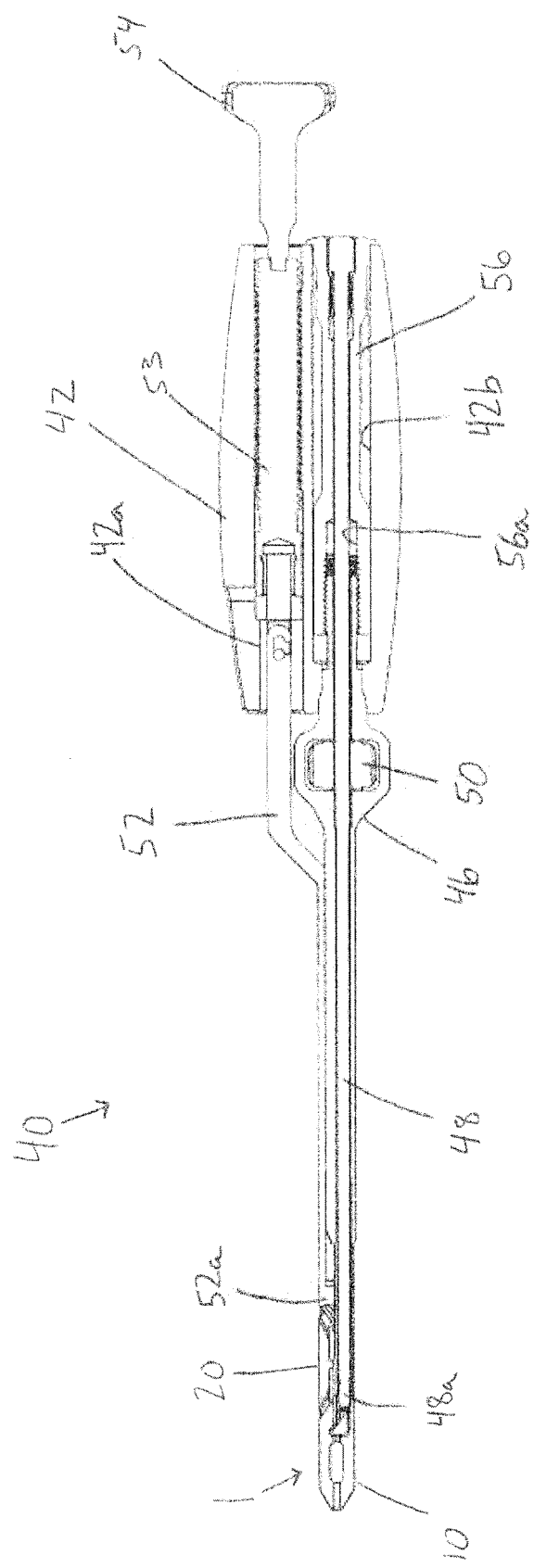
FIG. 8B is a longitudinal cross-sectional view of the device and tool of FIG. 8A.
Figure 9B:
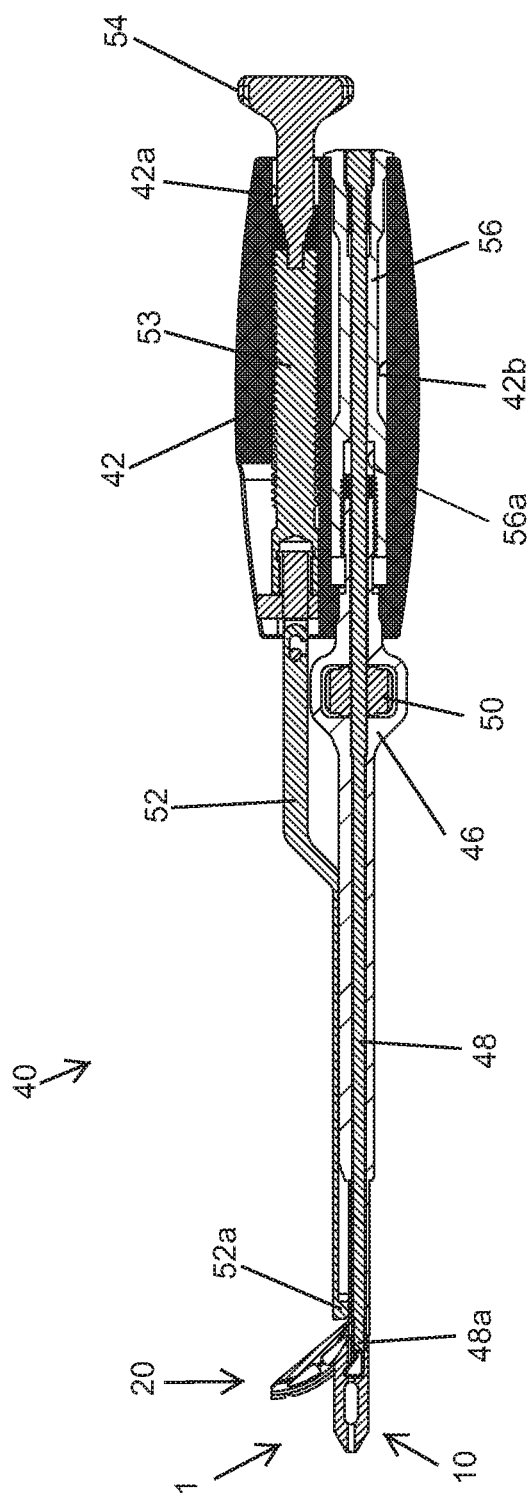
FIG. 9B is a longitudinal cross-sectional view of the device and tool of FIG. 9B.

FIGS. 8A, 8B show the operation of the tool 40 with the interbody device 1 connected to the tool in the insertion configuration and FIGS. 9A, 9B show the tool 40 and interbody device 1 in the expanded configuration. In operation, the interbody device 1 is attached to the distal holding portion 44 of the tool 40 with the interbody device in an unexpanded or compact insertion configuration with the first and second implant members in substantial alignment, i.e., lined up end to end to minimize the lateral width of the interbody device. Accordingly, substantial alignment means that the longitudinal axes $L_1$, $L_2$ of the first and second implant members should not meet at an angle of greater than 30 degrees, and more preferably intersect at an angle less than 15 degrees, and still more preferably at an angle less than 5 degrees. Alternatively, substantial alignment may be defined as alignment of the axes L1, L2 of the spacer members 10, 12 sufficient to allow the interbody device to be inserted into the intervertebral space through Kambin's triangle while avoiding necessitating bone removal for this purpose.

Figure 10A:
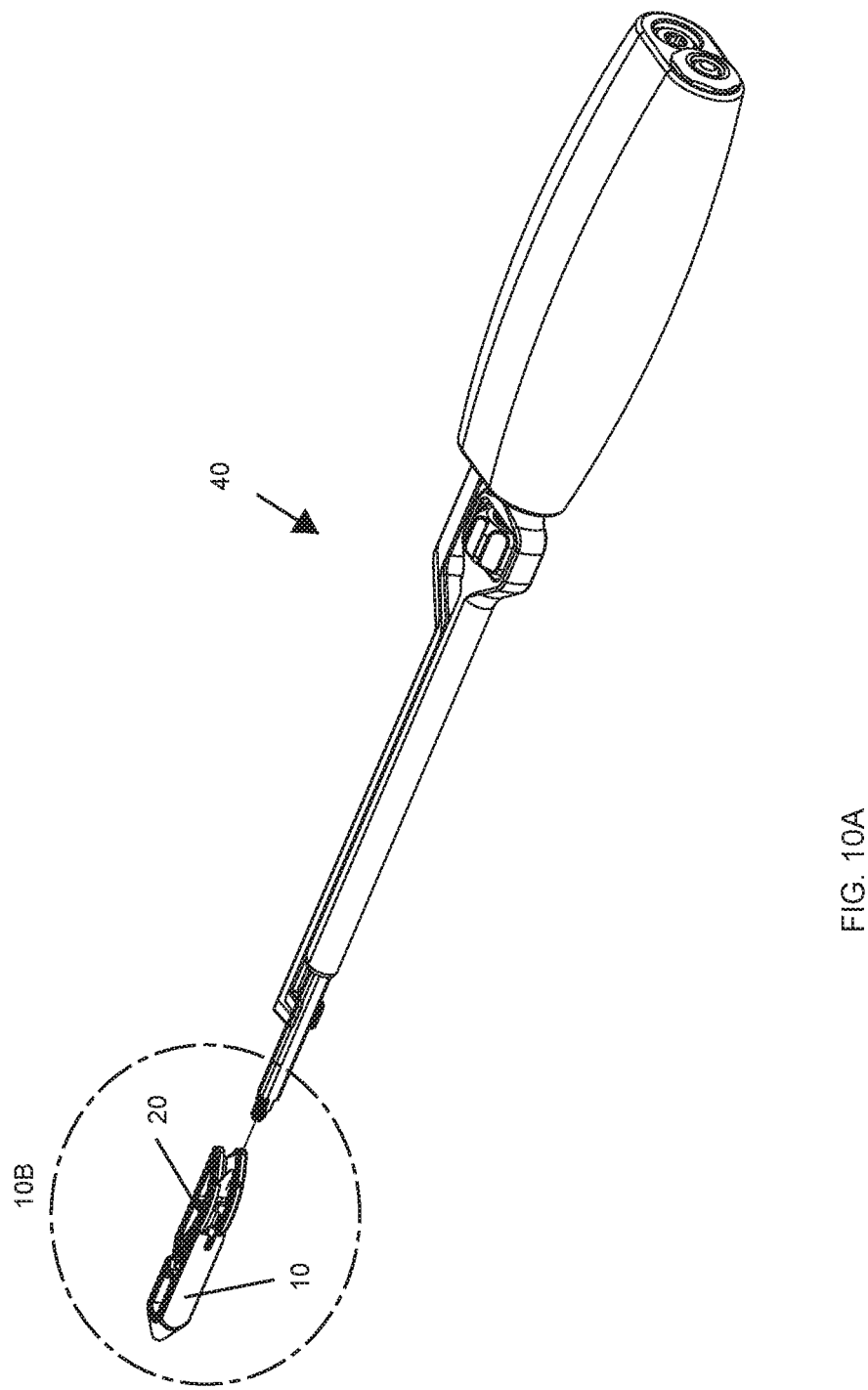
FIGS. 10A, 10B and 10C illustrate how the interbody device is connected to the insertion tool.
Figure 10C:
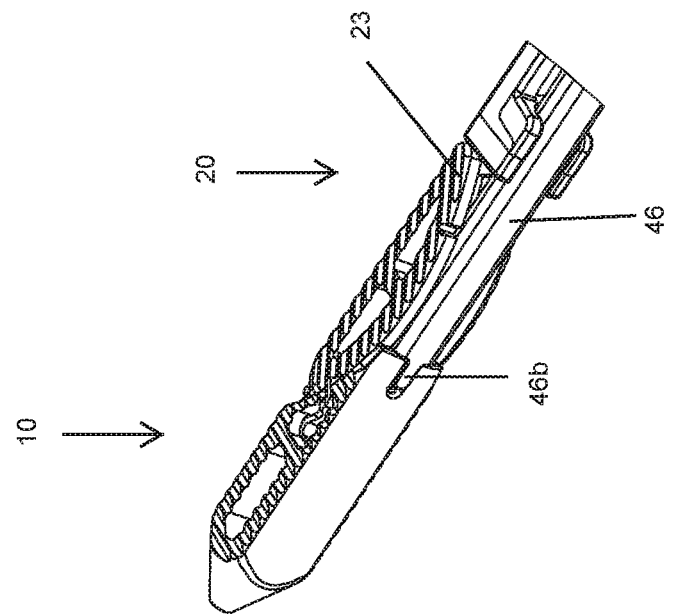
Figure 10B:
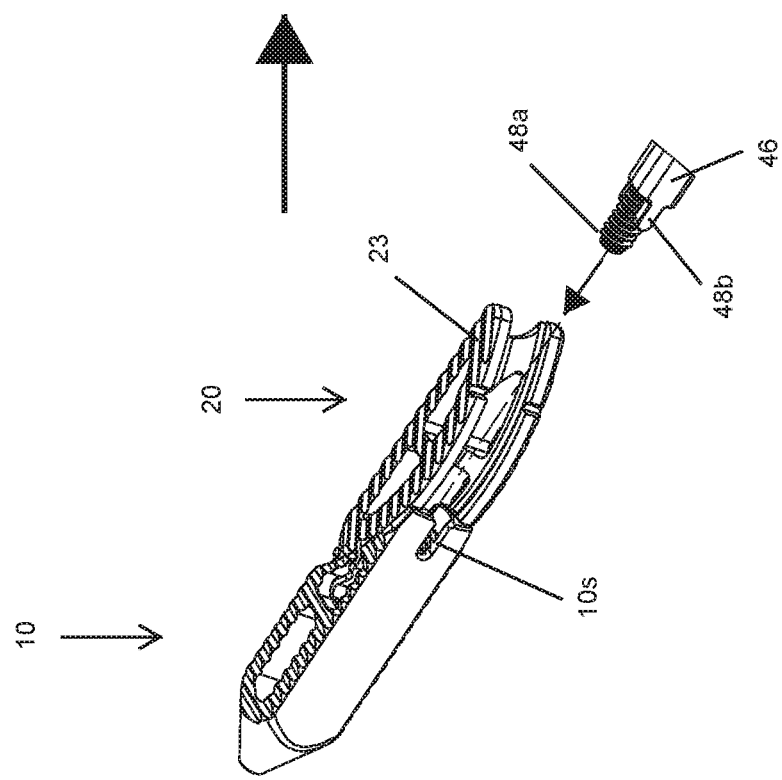
Figure 11:
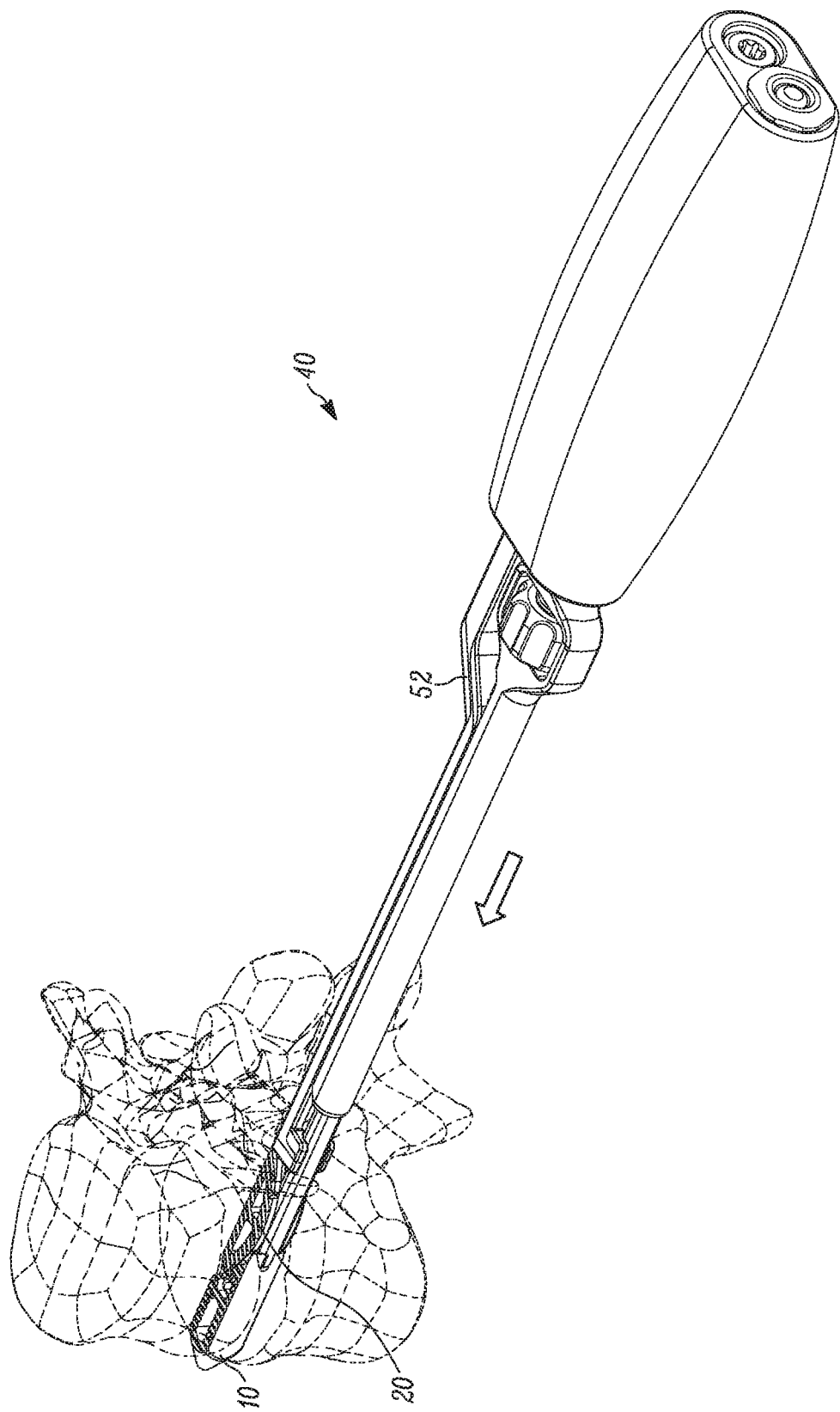
FIG. 11 illustrates one approach for inserting the interbody device into the intervertebral disc space with the insertion tool.
Figure 12:
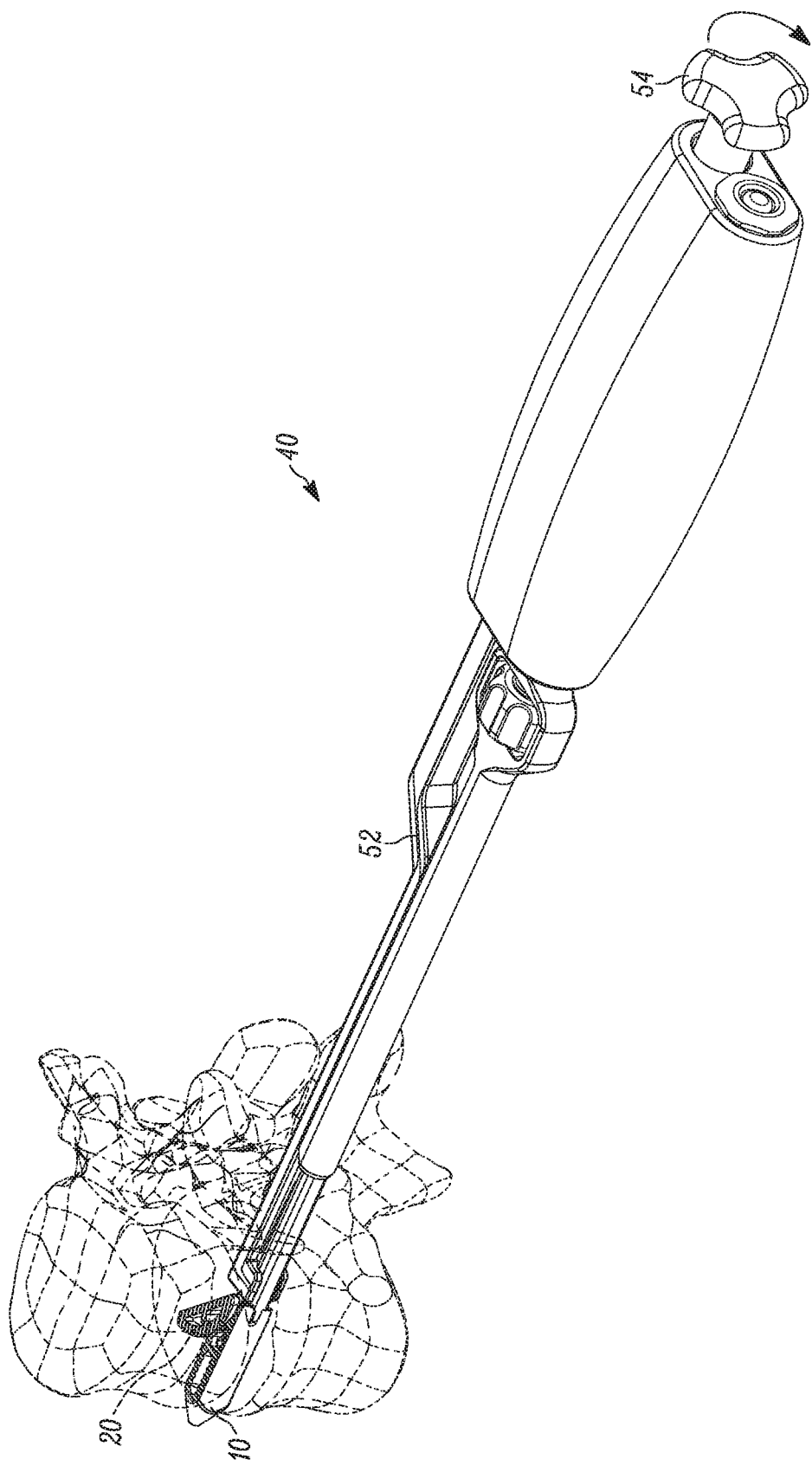
FIG. 12 illustrates expanding the interbody device in a lateral dimension within the intervertebral space via rotation of the tool knob.
Figure 13:
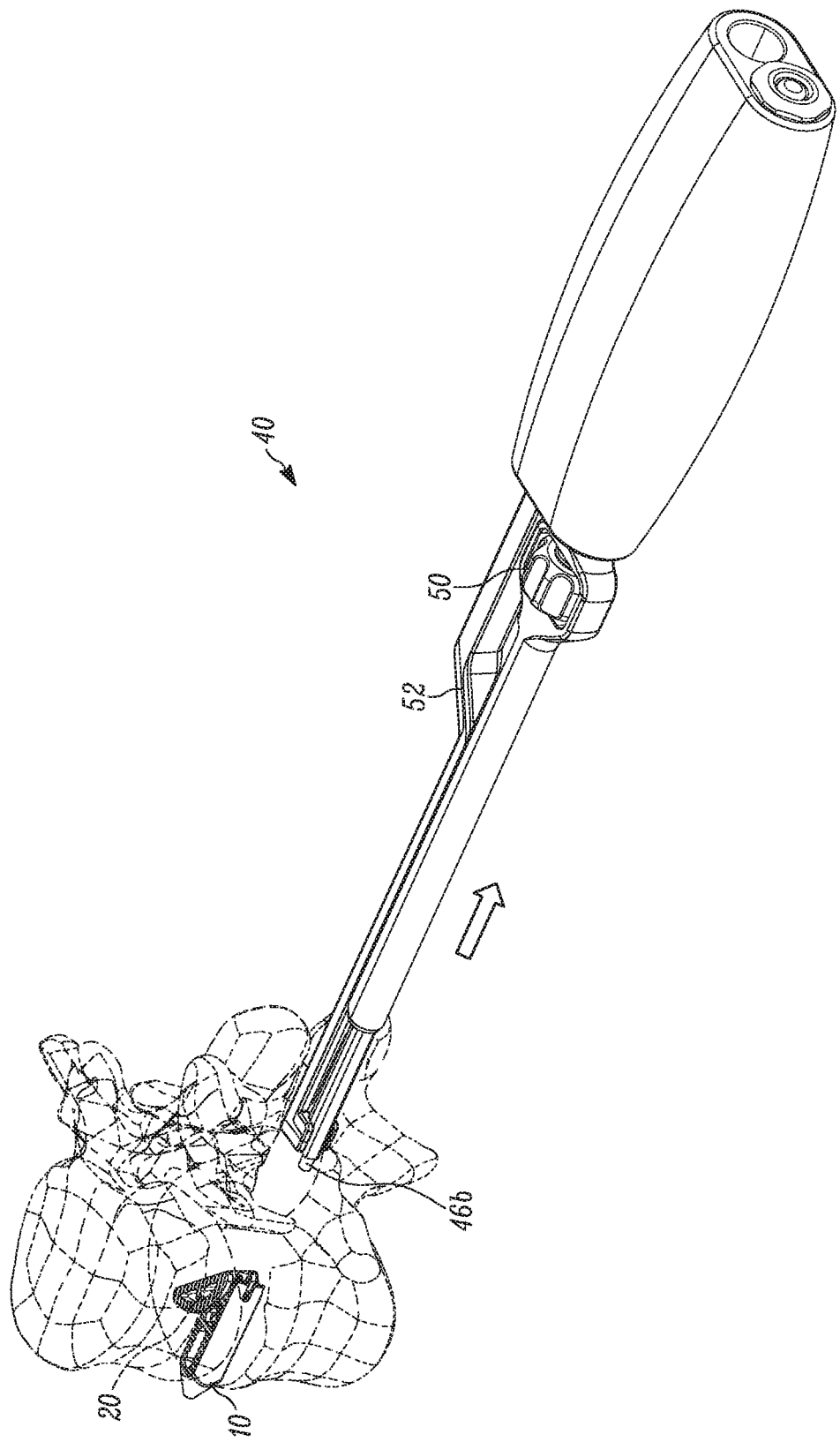
FIG. 13 illustrates the step of removing the inserter from the interbody device and the intervertebral space after the interbody device has been expanded.
Figure 14:
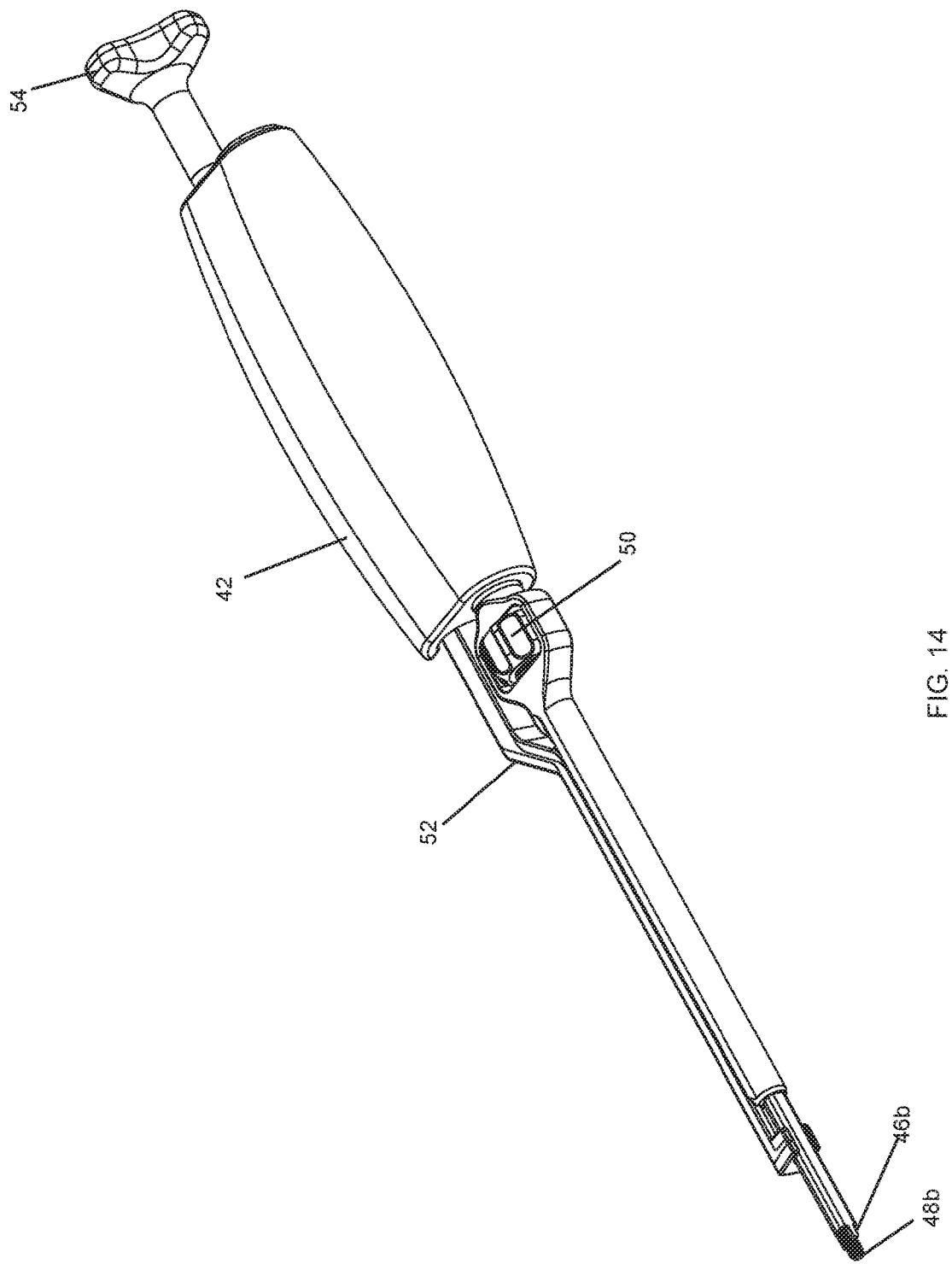
FIG. 14 is a perspective view of the insertion tool of FIG. 7.
Figure 15:
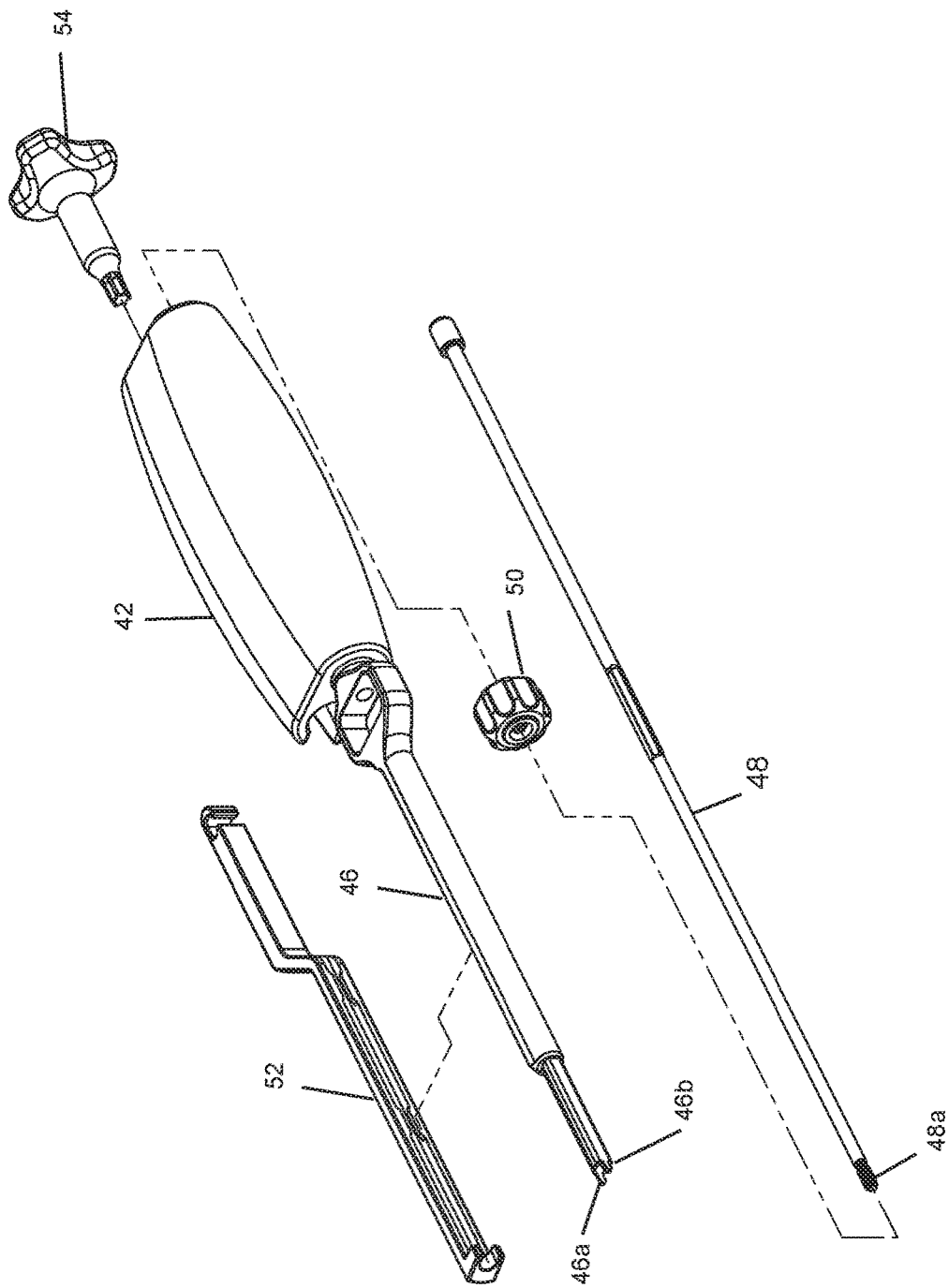
FIG. 15 illustrates the insertion tool of FIG. 7 disassembled for cleaning.
Figure 16A:
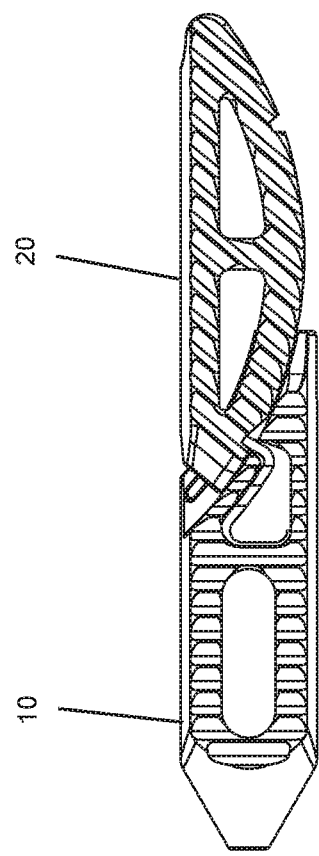
FIGS. 16A-C illustrate the interbody device in a compact non-expanded orientation.
Figure 16B:
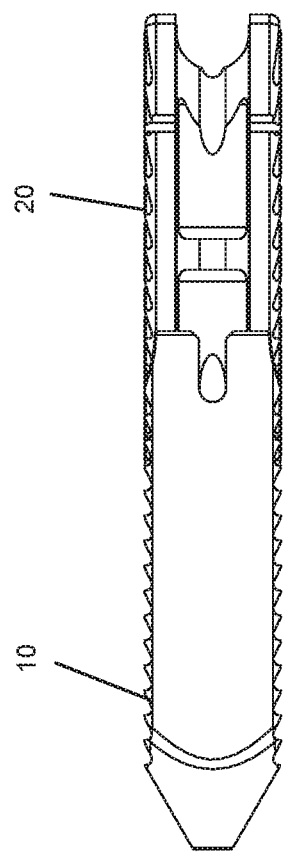
Figure 16C:
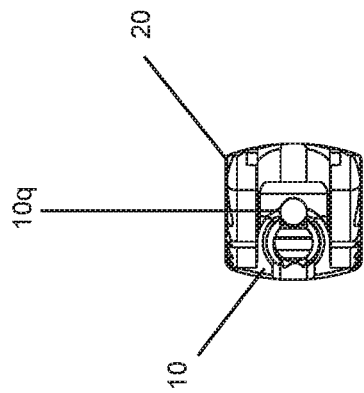

As shown in FIGS. 10B, 10C, the interbody device 1 is attached to the distal holding portion 44 by inserting the prongs 46a, 46b of the distal end of the stationary shaft into the slots 10s, 10t of the first implant member and threading the threaded end 48a of the draw rod 48 via clockwise rotation of the knob 50 into the threaded recess 10r within the cavity of the first implant member 10. Once the interbody device 1 is attached to the insertion tool 40, the second implant member 20 may be shifted to an expanded configuration via rotation of the rotatable knob 54 in a clockwise direction. Rotation of the knob 54 advances the ram member 52 longitudinally along the stationary shaft 46, causing the distal end of ram member 52a to urge the second implant member 20 distally along the arcuate path of the sliding interface 15. As the second implant member 20 is shifted along the arcuate path, the longitudinal axis $L_2$ of the second implant member 20 shifts out of substantial alignment with the longitudinal axis $L_1$ of the first implant member 10 to extend more transversely relative thereto, i.e., the angle between the axes is increased. The second implant member 20 is advanced until the retaining clip 30 blocks further movement of the second implant member 20 via abutting engagement with the stops 20n, 20p, or alternatively until the distal end of the ram member 52 abuts the first implant member 10, preventing further advancement of the ram member 52 relative to the spacer member 10. Once the second implant member 20 is advanced to the desired expanded position, the interbody device 1 may be removed from the tool 40 by rotating the knob 50 in a counterclockwise direction to rotate the draw rod 48 until the threaded end 48a is fully retracted from the threaded recess 10r of the first implant member.

In an alternative form, a tool for manipulating a surgical device is disclosed. In one embodiment, the tool takes the form of an anchor blade insertion tool 100 for manipulating an anchor blade, and particularly for inserting an anchor blade 150 into a retractor blade, such as that disclosed in FIG. 5 of United States Published Patent Application 2012/0232349, which is hereby incorporated by reference in its entirety. Although the tool is disclosed with reference to an anchor blade insertion tool, the tool has applicability in numerous applications, as would be apparent to one of ordinary skill in the art.

As shown in FIGS. 20-24 the insertion tool 100 includes a distal handle member 102, an actuator connected thereto in the form of a lever 104. The lever 104 is connected to a moveable lower shaft 106, which is operable in conjunction with a stationary upper shaft 108 for gripping and releasing a portion of a surgical device, such as an opening 150a in the proximal portion of anchor blade 150. The moveable lower shaft 106 is shiftable proximally and distally along a longitudinal tool axis L between gripping and releasing configurations via shifting of the lever 104 from a distal or forward position to a proximal or rearward position, respectively. In other words, the lever 104 is pulled back to release the anchor blade 150, and alternatively shifted forward to secure the anchor blade 150 to the tool 100.

Figure 21:
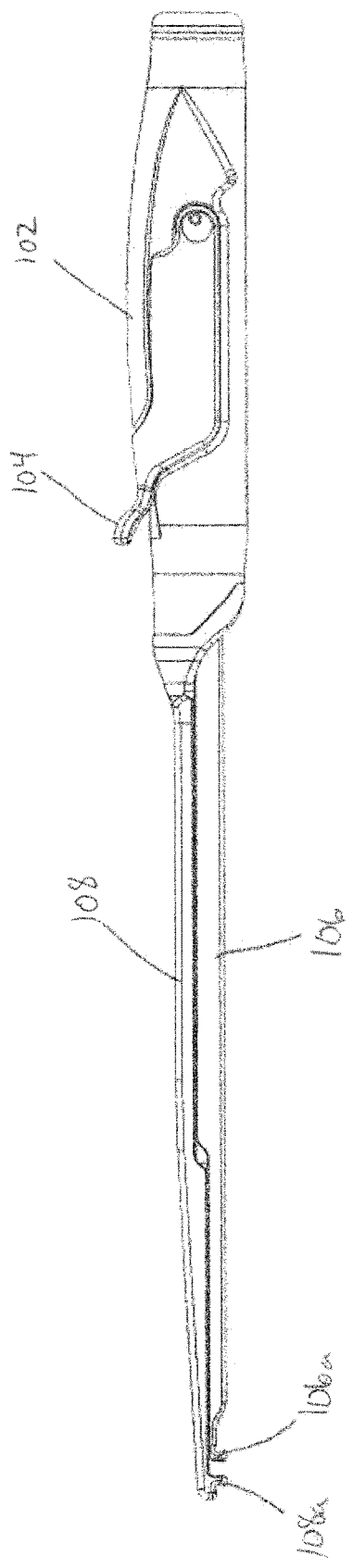
FIG. 21 is a lateral view of the anchor blade inserter of FIG. 20.
Figure 22:
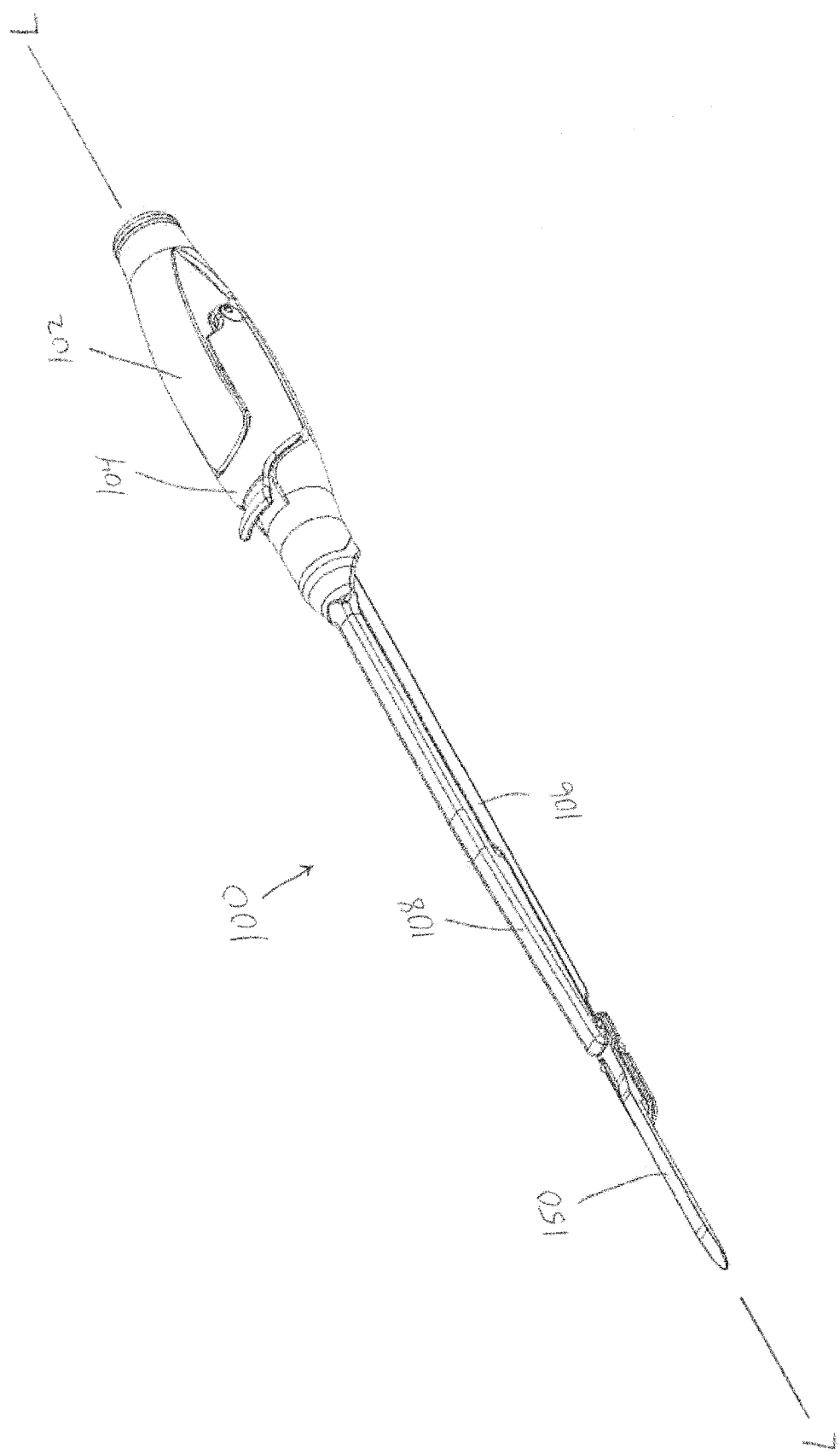
FIG. 22 is a perspective view of the anchor blade inserter of FIG. 20 holding an anchor blade in a first gripping orientation.
Figure 23:
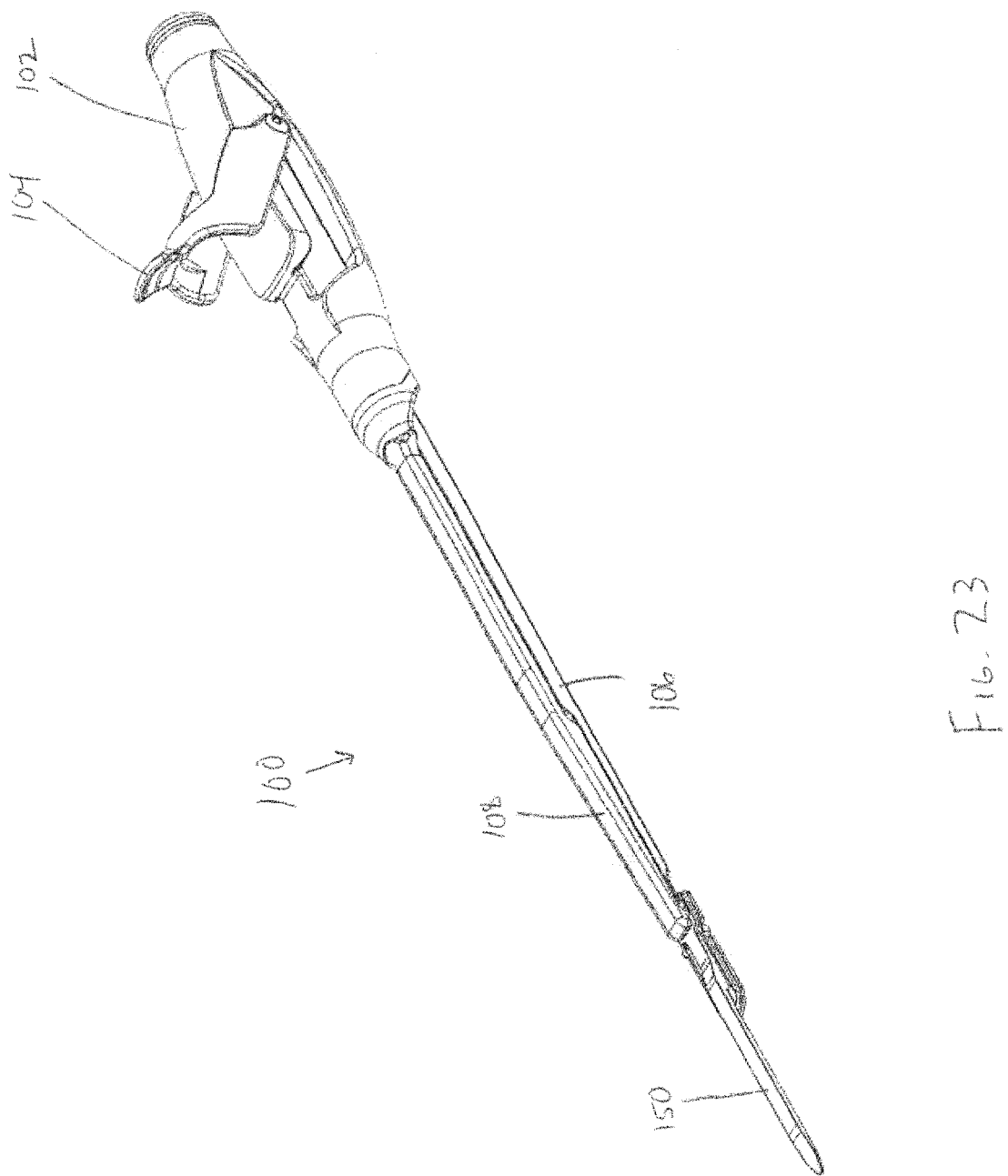
FIG. 23 is a perspective view of the anchor blade inserter in an intermediate partial release orientation.

Each of the upper and lower shafts 108, 106 include a gripping portion at the distal end thereof in the form of a gripping hook 108a, 106a. The stationary distal gripping hook 108a of the upper shaft 108 is located distally along the tool axis L from the gripping hook 106a of the moveable lower shaft 106. The gripping hooks 106a, 108a are configured to fit within a throughbore or other structure with opposing surfaces that can be gripped via expansion of the gripping hooks apart from one another. Because the gripping hooks are configured to fit between opposing surfaces, the hooks face away from one another with the distal gripping hook 108a extending distally, and the proximal movable gripping hook 106a extending proximally as shown in FIG. 21.

The moveable lower shaft 106 is connected to the lever 104 via a linkage 110. The linkage is preferably comprised of a material with superelastic characteristics, such as NITINOL. The operation and characteristics of such a superelastic linkage is described in United States Published Patent Application 2009/0234395, which is hereby incorporated by reference in its entirety. Such a linkage is preferred to transmit relatively large amounts of tensile force with minimal displacement/strain of the linkage 110. The linkage 110 is connected to the lever 104 via connecting members 112 and 114. Cylindrical connecting member 114 is connected to the lever 104 via a pin 116 which extends through a transverse through-opening 114a. The through-opening 114a is sized and configured to accommodate arcuate movement of the pin 116 by allowing the pin 116 to travel normally (i.e. up and down) with respect to the longitudinal tool axis. The lever 104 includes opposing pivot portions 104a, 104b with recesses 104c, 104d that are configured to hold the pin 116 therebetween. The pin 116 is thereby held offset from the axis of rotation of the pivot portions 104a, 104b such that when the lever 104 is rotated clockwise about the pivot portions' axis of rotation, the pin 116 rotates clockwise about the lever axis of rotation and experiences displacement towards the distal end of the tool. This reduces tension on the linkage 110 and also urges the linkage 110 distally to cause a corresponding distal movement of the lower shaft member 106, thereby moving the proximal gripping hook 106a to move towards the stationary gripping hook 108a of the upper shaft 108 into the releasing or loading configuration. To return the tool to the gripping configuration, the lever 104 is returned to the forward position as shown in FIG. 21. This pulls the lower shaft 106 proximally and puts the linkage 110 in tension with an appropriate amount of force suitable for holding and manipulating the anchor blade 150.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. An expandable intervertebral device for implantation within an intervertebral space between adjacent vertebrae, the expandable intervertebral device comprising:

a first leading bearing member and a second trailing bearing member connected to the first leading bearing member each having a longitudinal axis and opposing bone-engaging outer surfaces extending between a distal leading end and a proximal trailing end; and connecting portions of the first and second bearing members configured for allowing the first and second members to stay connected while shifting relative to each other;

wherein the first leading bearing member comprises an insertion tool engaging portion at the trailing end thereof configured to be fixed to an insertion tool and the second trailing bearing member is configured to allow the insertion tool to extend through at least a portion thereof to access the insertion tool engaging portion to allow the first leading bearing member to be fixed to the insertion tool at the insertion tool engaging portion and to allow the second trailing bearing member to be shifted relative to the first leading bearing member and the insertion tool while the first leading bearing member is fixed to the insertion tool.

2. The expandable intervertebral device of claim 1, wherein the first and second bearing members are configured to shift relative to each other between:
(1) an unexpanded insertion configuration, wherein the trailing end of the first leading bearing member is engaged with the leading end of the second trailing bearing member and the longitudinal axes of the first and second bearing members are substantially aligned, and
(2) an expanded configuration, wherein the leading end of the second trailing bearing member is shifted away from the trailing end of the first leading bearing member so as to be spaced in a lateral direction from the trailing end of the first leading bearing member.

3. The expandable intervertebral device of claim 1, wherein the connecting portions have an arcuate configuration.

4. The expandable intervertebral device of claim 1, wherein the connecting portions comprise mating projecting and recess portions of the first and second bearing members that are configured to allow the projecting portion to slide in the recess portion as the second trailing bearing member is shifted relative to the first leading bearing member.

5. The expandable intervertebral device of claim 1, further comprising a resilient retaining clip operably connected to one of the first and second bearing members for limiting the movement of the second trailing bearing member with respect to the first leading bearing member.

6. The expandable intervertebral device of claim 1, wherein the first and second bearing members comprise an opening extending along the longitudinal axes thereof sized and configured to allow a guidewire to pass through the bearing members.

7. The expandable intervertebral device of claim 1, wherein the opposing outer surfaces of the first leading bearing member comprise projections that are configured to resist migration in one direction, and the opposing outer surfaces of the second trailing bearing member comprise projections that are configured to resist migration in a different direction from the projections of the opposing outer surfaces of the first leading bearing member.

8. The expandable intervertebral device of claim 1, wherein at least one of the first and second bearing members comprise a through-opening in each of the opposing bone-engaging outer surfaces to allow boney ingrowth therein.

9. The expandable intervertebral device of claim 1, wherein the connecting portion of the second trailing bearing member extends from the leading end to the trailing end thereof.

10. The expandable intervertebral device of claim 1, wherein the connecting portions of the first and second bearing members comprise upper and lower arcuate ridges of one of the first and second bearing members that are received in corresponding upper and lower arcuate channels of the other of the first and second bearing members.

11. The expandable intervertebral device of claim 1, wherein the insertion tool engaging portion includes a threaded recess for engaging with a corresponding threaded rod of the insertion tool to fix the first leading bearing member thereto.

12. The expandable intervertebral device of claim 1, wherein the second trailing bearing member includes a lateral opening on one side thereof to allow the insertion tool to be inserted through the lateral opening to hold the first leading bearing member while further allowing the second trailing bearing member to be shifted laterally while the first leading bearing member is held by the insertion tool.

13. An insertion tool for implanting a laterally expandable interbody device having interconnected first and second bearing members between adjacent upper and lower vertebrae, comprising:
a proximal handle;
a distal holding portion of the insertion tool configured for fixing the first bearing member of the interbody device to the insertion tool such that the first bearing member is kept from shifting with respect to the insertion tool; and
an actuator for engaging with the second bearing member for shifting the second bearing member laterally with respect to the first bearing member while the first bearing member is fixed to the insertion tool at the distal holding portion for expanding the interbody device laterally.

14. The insertion tool of claim 13, wherein the distal holding portion further comprises a threaded rod configured to matingly engage with a threaded recess of the first bearing member to attach the expandable interbody device to the insertion tool.

15. The insertion tool of claim 13, wherein the actuator is configured to shift proximally and distally along a longitudinal tool axis and abbutingly engage a proximal end of the second bearing member to shift the second bearing member from an unexpanded orientation to a laterally expanded orientation with respect to the first bearing member.

16. The insertion tool of claim 15, wherein the actuator is a ram member operably connected to a rotatable knob that is operable to cause the ram member to shift along the longitudinal axis when the knob is rotated.

17. The insertion tool of claim 14, further comprising a rotatable knob operably connected to the threaded rod for rotating the threaded rod to matingly engage or disengage with the threaded recess of the first bearing member.

18. The insertion tool of claim 13, further comprising a stationary shaft connected to the proximal handle and to which the actuator is shiftably connected.

19. The insertion tool of claim 18, wherein the stationary shaft comprises a distal alignment feature in the form of at least one prong for engaging with at least one corresponding mating slot of the first bearing member.

20. The insertion tool of claim 18, further comprising a threaded rod rotatably disposed within the stationary shaft for matingly engaging with a threaded recess of the first bearing member to attach the expandable interbody device to the insertion tool.

21. An expandable intervertebral device for implantation within an intervertebral space between adjacent vertebrae, the expandable intervertebral device comprising:
a first leading bearing member and a second trailing bearing member connected to the first leading bearing member each having a longitudinal axis extending between a distal leading end and a proximal trailing end; and
a cam interface between the first and second bearing members configured for allowing the first and second members to stay connected while shifting relative to each other, the cam interface configured such that a longitudinally directed force aligned with the longitudinal axis of the first leading bearing member applied to the trailing end of the second trailing bearing member causes the second trailing bearing member to shift along a path transverse to the longitudinally directed force.

22. The expandable intervertebral device of claim 21, wherein the cam interface comprises mating cam surfaces and cam follower surfaces of the first and second bearing members.

23. The expandable intervertebral device of claim 21, wherein the cam interface includes an arcuate trailing end portion of the first leading bearing member and a corresponding arcuate connecting portion of the second trailing bearing member, such that the second trailing bearing member shifts along an arcuate path when the longitudinally directed force is applied to the trailing end of the second trailing bearing member.

24. The expandable intervertebral device of claim 23, wherein the arcuate connecting portion of the second trailing bearing member extends from the distal leading end to the proximal trailing end thereof.

25. The expandable intervertebral device of claim 21, wherein the first and second members are configured to shift relative to each other between:
(1) an unexpanded insertion configuration, wherein the trailing end of the first leading bearing member is engaged with the leading end of the second trailing bearing member and the longitudinal axes of the first and second bearing members are substantially aligned, and
(2) an expanded configuration, wherein the leading end of the second trailing bearing member is shifted away from the trailing end of the first leading bearing member so as to be spaced in a lateral direction from the trailing end of the first leading bearing member.

26. The expandable intervertebral device of claim 21, wherein the first leading bearing member comprises an insertion tool engaging portion at the trailing end thereof and the second trailing bearing member is configured to allow an insertion tool to extend through at least a portion thereof to access the insertion tool engaging portion.

27. A method of expanding an expandable intervertebral device having interconnected first and second bearing members each having a longitudinal axis extending between leading and trailing ends thereof, comprising:
positioning the first and second bearing members in an aligned, unexpanded orientation with the longitudinal axes of the first and second bearing members in general alignment with one another; and
shifting the first and second bearing members to an unaligned, expanded orientation by applying a longitudinally directed force aligned with the longitudinal axis of the first bearing member to the trailing end of the second bearing member to cause the second bearing member to shift relative to the first bearing member along a path transverse to the longitudinally directed force.

28. The method of claim 27, wherein the second bearing member is shifted along an arcuate path by the longitudinally directed force.

29. The method of claim 27, further comprising holding the first bearing member with an insertion tool while applying the longitudinally directed force to the second bearing member.

30. The method of claim 27, further comprising withdrawing application of the longitudinally directed force when the second bearing member is shifted to the expanded orientation with the leading end of the second bearing member spaced laterally from the trailing end of the first bearing member.

31. The method of claim 30, wherein when the second bearing member is shifted to the expanded orientation, a retaining clip of the first bearing member engages with a mating recess in the second bearing member to keep the second bearing member from shifting relative to the first bearing member.

32. The method of claim 27, further comprising applying the longitudinally directed force by shifting a moveable ram member along a longitudinal axis of an insertion tool.

33. The method of claim 27, wherein shifting the first and second bearing members to an unaligned, expanded orientation is accomplished without changing the direction of the applied longitudinally directed force as the second bearing member shifts.

* * * * *